(12) United States Patent
Madabhushi et al.

(10) Patent No.: US 10,540,570 B2
(45) Date of Patent: Jan. 21, 2020

(54) PREDICTING PROSTATE CANCER RECURRENCE IN PRE-TREATMENT PROSTATE MAGNETIC RESONANCE IMAGING (MRI) WITH COMBINED TUMOR INDUCED ORGAN DISTENSION AND TUMOR RADIOMICS

(71) Applicant: Case Western Reserve University, Cleveland, OH (US)

(72) Inventors: Anant Madabhushi, Shaker Heights, OH (US); Rakesh Shiradkar, Cleveland, OH (US); Soumya Ghose, University Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 106 days.

(21) Appl. No.: 15/923,495

(22) Filed: Mar. 16, 2018

(65) Prior Publication Data

US 2018/0276498 A1    Sep. 27, 2018

Related U.S. Application Data

(60) Provisional application No. 62/474,290, filed on Mar. 21, 2017.

(51) Int. Cl.
*G06K 9/62* (2006.01)
*A61B 5/00* (2006.01)
(Continued)

(52) U.S. Cl.
CPC ............ *G06K 9/6227* (2013.01); *A61B 5/055* (2013.01); *A61B 5/4381* (2013.01);
(Continued)

(58) Field of Classification Search
None
See application file for complete search history.

(56) References Cited

U.S. PATENT DOCUMENTS 5,993,388 A * 11/1999 Kattan .................. G06G 1/001
128/898
2012/0329713 A1* 12/2012 Klem ............... G01N 33/57434
514/9.7
(Continued)

OTHER PUBLICATIONS

Shah, Vijay, et al. "Decision support system for localizing prostate cancer based on multiparametric magnetic resonance imaging." Medical physics 39.7Part1 (2012): 4093-4103. (Year: 2012).*
(Continued)

*Primary Examiner* — Samah A Beg
(74) *Attorney, Agent, or Firm* — Eschweiler & Potashnik, LLC

(57) ABSTRACT

Embodiments predict prostate cancer (PCa) biochemical recurrence (BCR) employing an image acquisition circuit that accesses a first pre-treatment image and a second pre-treatment image of a region of tissue demonstrating PCa, a distension feature circuit that extracts a set of distension features from the first pre-treatment image, and computes a first probability of PCa BCR based on the set of distension features, a radiomics circuit that extracts a set of radiomics features from the second pre-treatment image, and computes a second probability of PCa recurrence based on the set of radiomics feature, a combined tumor induced organ distension with tumor radiomics (COnTRa) circuit that computes a joint probability that the region of tissue will experience PCa BCR based on the first probability and the second probability, and a display circuit that displays the joint probability.

20 Claims, 10 Drawing Sheets

(51) Int. Cl.
*G06T 7/11* (2017.01)
*G06T 7/174* (2017.01)
*G06T 7/33* (2017.01)
*G06K 9/68* (2006.01)
*A61B 5/055* (2006.01)

(52) U.S. Cl.
CPC .......... *A61B 5/4842* (2013.01); *A61B 5/7267* (2013.01); *G06K 9/6221* (2013.01); *G06K 9/685* (2013.01); *G06T 7/11* (2017.01); *G06T 7/174* (2017.01); *G06T 7/337* (2017.01); *G06T 2207/10096* (2013.01); *G06T 2207/20076* (2013.01); *G06T 2207/20081* (2013.01); *G06T 2207/30081* (2013.01); *G06T 2207/30096* (2013.01)

(56) References Cited

U.S. PATENT DOCUMENTS

| | | | | |
|---|---|---|---|---|
| 2013/0059755 A1* | 3/2013 | Talantov | .......... | G01N 33/57434 506/9 |
| 2013/0323739 A1* | 12/2013 | Klem | ................. | G01N 33/5091 435/6.12 |
| 2016/0196647 A1* | 7/2016 | Madabhushi | ........ | A61B 5/4381 |
| 2017/0084021 A1* | 3/2017 | Athelogou | ............ | G06T 7/0012 |
| 2018/0276497 A1* | 9/2018 | Madabhushi | ........ | G06K 9/6227 |
| 2018/0336395 A1* | 11/2018 | Madabhushi | ...... | G06K 9/00147 |
| 2019/0251687 A1* | 8/2019 | Madabhushi | ........ | G06K 9/0014 |

OTHER PUBLICATIONS

Shukla-Dave, Amita, et al. "Prediction of prostate cancer recurrence using magnetic resonance imaging and molecular profiles." Clinical Cancer Research 15.11 (2009): 3842-3849. (Year: 2009).*

Stamatakis, Lambros, et al. "Accuracy of multiparametric magnetic resonance imaging in confirming eligibility for active surveillance for men with prostate cancer." Cancer 119.18 (2013): 3359-3366. (Year: 2013).*

* cited by examiner

PREDICTING PROSTATE CANCER RECURRENCE IN PRE-TREATMENT PROSTATE MAGNETIC RESONANCE IMAGING (MRI) WITH COMBINED TUMOR INDUCED ORGAN DISTENSION AND TUMOR RADIOMICS

CROSS REFERENCE TO RELATED APPLICATIONS

This application claims the benefit of U.S. Provisional Application 62/474,290, filed Mar. 21, 2017.

FEDERAL FUNDING NOTICE

The invention was made with government support under 1R01CA208236-01A1 awarded by the National Institute of Health National Cancer Institute. The government has certain rights in the invention.

BACKGROUND

Magnetic resonance (MR) imaging (MRI) is routinely used to diagnose prostate cancer (PCa) and identify the stage of PCa. PCa may induce changes in the shape of the prostate capsule and central gland (CG) in biopsy positive (Bx+) patients relative to biopsy negative (Bx−) patients, elevated-prostate specific antigen (PSA) patients, or normal patients. PCa may also induce changes in the volume of the prostate and CG in Bx+ patients relative to Bx− patients, elevated-PSA patients, and normal patients. These changes in the shape and volume of the prostate may be observed in T2 weighted (T2w) MRI images.

Radiation therapy and radical prostatectomy are common treatments for PCa, with over 50% of PCa patients being treated with either or both treatments. However, radiation therapy has a failure rate as high as 25%, and 30-35% of treated PCa patients experience treatment failure within ten years. Predicting biochemical recurrence (BCR) prior to treatment may enable better planning and personalization of treatment. MR images may be used to assist the prediction of BCR in PCa patients. However, when obvious extra-capsular spread of the disease is not present, conventional approaches employing MRI are not useful for distinguishing patients who will experience BCR from those who will not.

Multi-parametric MRI (mpMRI) is widely used in the management of PCa to improve the detection, tumor staging, and risk stratification for selection of patients for active surveillance and recurrence prediction of the disease. Despite its broad adoption in the management of PCa, conventional approaches for predicting BCR using MRI, including mpMRI, are susceptible to variability in MRI acquisition parameters, scanner protocols, image artifacts, and non-standardized image intensities. This variability may occur both within an individual institution (e.g., hospital, university) and across multiple institutions. Conventional approaches to MRI-based PCa diagnosis, identification, or prognosis prediction may employ protocols or guidelines for imaging acquisition parameters and findings reporting, although score interpretation and detection thresholds, particularly across multiple institutions, have not been uniformly applied or exhaustively studied. Furthermore, implementing protocols and guidelines across different institutions takes time, costs money, and puts a patient at additional risk if the guidelines and protocols are not consistently applied.

Radiomics or computer extracted texture features have been used to characterize tumor presence on MRI images. Radiomics-based approaches quantify sub-visual patterns represented in radiological images, including MRI images. However, texture analysis does not always allow for discrimination between more and less aggressive disease. Conventional radiomics-based approaches may also suffer reduced BCR predictive accuracy caused by inter-protocol misalignment, image acquisition artifacts and non-standardized image intensities.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
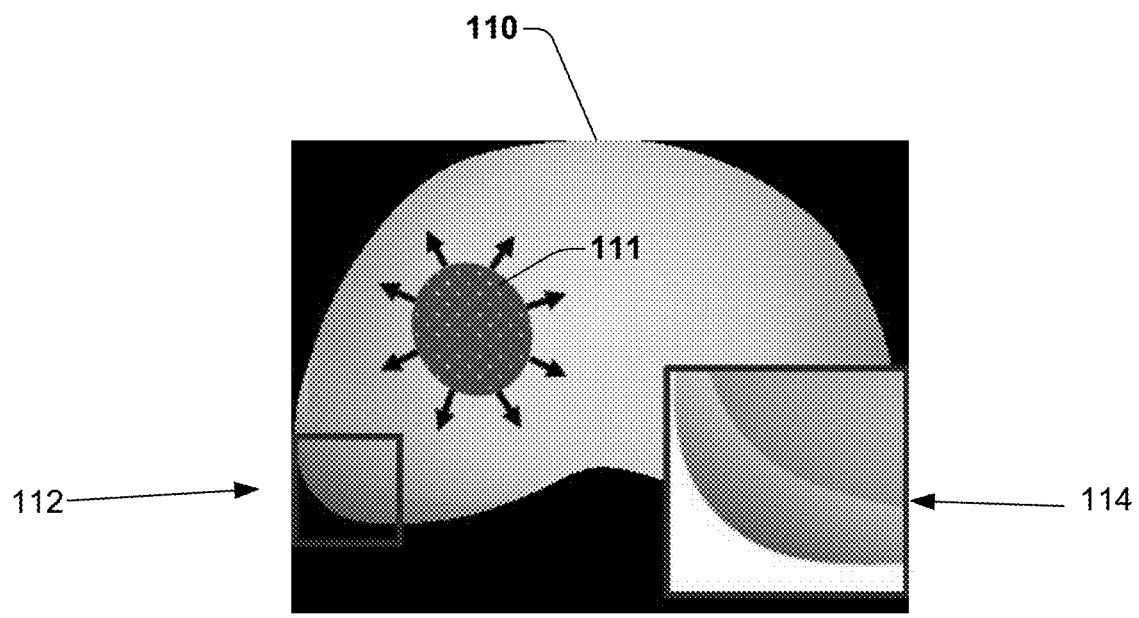
FIG. 1 illustrates tumor induced distension in similar prostates.
Figure 1:
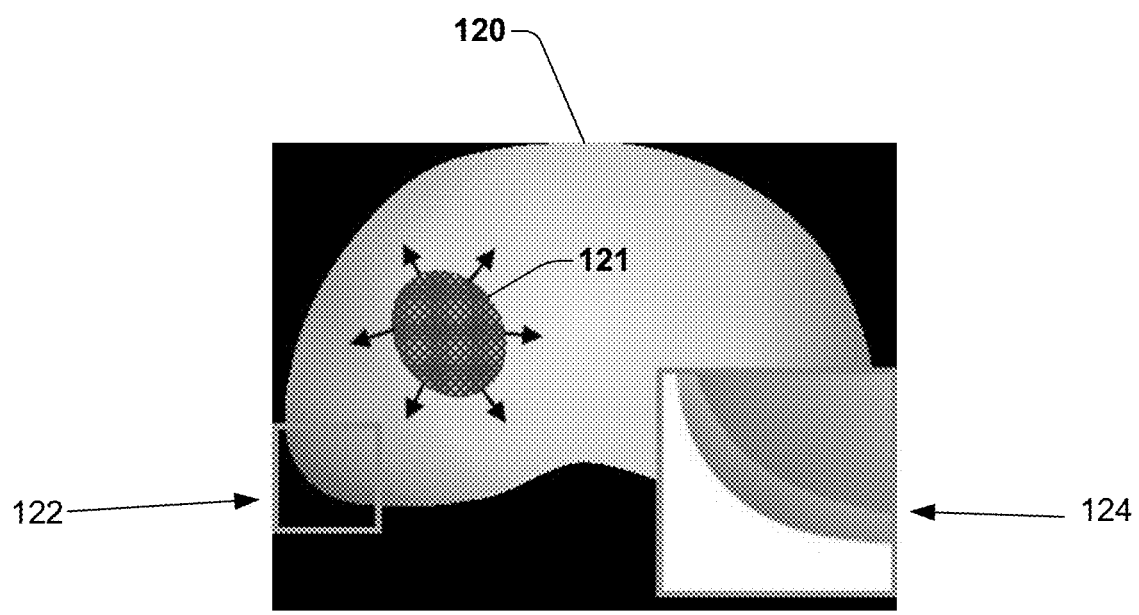

Embodiments identify prostate cancer patients at risk of BCR using a combined tumor induced organ distension with tumor radiomic (COnTRa) feature approach. Embodiments extract a set of distension features from a surface of interest (SOI) of a region of tissue demonstrating PCa represented in multi-parametric MRI imagery, and a set of radiomic features from the region of tissue. Radiomics, as used herein, refers to the quantitative extraction of histogram, and/or texture-based features from radiographic images to distinguish disease phenotypes that are not visually appreciable on imaging. Embodiments compute a first probability of BCR based on the set of distension features, and compute a second probability of BCR based on the set of radiomic features. Embodiments then compute a joint probability of BCR based on the first probability and the second probability. Embodiments using the joint probability predict BCR with an area under the receiver operating characteristic curve (AUC) of at least 0.84, which is higher than the AUC of either the first probability or the second probability, or of conventional approaches. Embodiments further provide a statistically significant (p=0.01) separation in the predicted survival time between the two classes of patients (BCR−, BCR+). Embodiments may also construct a BCR+ atlas, a BCR− atlas, generate an SOI mask based on the BCR+ atlas and BCR− atlas, and train a machine learning classifier to predict BCR using distension features and radiomic features.

Of the 180,890 new cases of prostate cancer diagnosed in USA in 2016 over 50% of these patients will be treated with either radical prostatectomy or radiation therapy or both. Despite advancement in treatment there is treatment failure in an estimated 30-35% of the treated prostate cancer patients within 10 years of treatment. An elevated prostate specific antigen (PSA) of 0.2 ng/ml for surgery or 2 ng/ml for radiation therapy above the nadir is indicative of treatment failure or BCR. BCR is often associated with the presence of more aggressive metastatic prostate cancer and hence a worse prognosis. Embodiments described herein detect or predict with greater accuracy than conventional approaches BCR in patients with prostate cancer undergoing definitive therapy and facilitate identifying patients who would benefit from adjuvant or neo-adjuvant therapies, or other types of therapy.

Multi-parametric magnetic resonance imaging (mpMRI) may be used for PCa detection, tumor staging, risk stratification for selection of men for active surveillance, and recurrence prediction. Radiomics or computer extracted texture features provide alternative feature representations and may be used for risk characterization and disease diagnosis. Radiomic features extracted from prostate tissue images in T2w MRI may be predictive of BCR. However, radiomic features extracted from mpMRI are susceptible to scanner variations, variations in acquisition protocols, image artifacts, and non-standardized image intensities.

Aggressive prostate cancer may induce organ distensions. For example, a tumor that is expanding and growing might be inducing stresses on the surrounding tissue which in turn might ripple over to the surface of the capsule. Thus a tumor field effect may manifest in the form of distensions to the capsule surface, and more and less aggressive tumors might differentially distend the capsule surface. On a T2w MRI scan, this distension may present as an irregular bulge and focal capsular retraction. Differences may manifest in the surface of the prostate capsule between prostates with or without cancer. FIG. 1 illustrates tumor induced distension in similarly shaped prostates 110 and 120. Prostate 110 is a BCR+ prostate. Prostate 120 is a BCR− prostate. A region of distension 112 induced by a tumor 111 in a BCR+ prostate 110 is magnified at 114. A region of distension 122 induced by a tumor 121 in BCR− prostate 120 is magnified at 124.

Embodiments described herein extract distension features and radiomic features from MRI imagery of cancerous prostates. Embodiments compute first probability of BCR based on the distension features, and a second probability of BCR based on the radiomics features. Embodiments compute a joint probability based on a Bayesian fusion of the class conditional probabilities. In one embodiment, two classes C+ and C− that represent more (e.g., BCR+) and less (e.g., BCR−) aggressive disease types which need to be distinguished are defined. Features that quantify organ distension $F_S$ and tumor radiomic features $F_R$ are extracted from MRI imagery. To quantify differences in organ distension between C+ and C−, a surface of interest (SOI) is defined that captures regions with significant differences between the two classes. Since the distension does not manifest across the entire organ surface, metrics used to capture the distension are limited to the SOI. The SOI is identified during a training phase as the region on the cancerous prostate capsule surface where the most differential distension between the recurrent and non-recurrent prostates is observed.

An atlas is a representative model of specific characteristics of a given population. A visual anatomic atlas of an organ for a specific class can be generated by registering individual 3D gland volume meshes to a representative template. The gland volume mesh Vp for a patient may be obtained from segmentation on an MRI image sequence that contains sufficient anatomic detail. The median volume mesh Vp from each class is chosen as a representative template to which individual Vp are registered to generate an atlas A for the respective class via affine registration followed by a B− spline registration. Atlases A+ and A− are generated for C+ and C−.

In one embodiment, an SOI is generated from the difference atlas $A_A$, which is obtained by comparing A+ and A− post co-registration. All registered masks of A+ and A− atlases are converted to signed distance maps in the registered space. As opposed to the binary representation of a mask where each voxel within the prostate capsule has a value of 1 and a value of 0 outside the capsule, the value assigned to each voxel is determined based off the distance of a given voxel from the capsule boundary. Consequently, the signed distance function yields positive values for voxels inside the prostate capsule, while the value of the voxel decreases as it approaches the boundary where the signed distance function is zero, becomes negative outside the prostate capsule, and continues to decrease depending on the distance of the voxel from the prostate capsule. A Generalized Linear Model (GLM) based T-test is performed with 5000 iterations using the signed distances at each voxel to obtain p− values. Vertices that have p<0.05 are considered statistically significant and identified as belonging to the SOI. The SOI for a patient is now obtained by inverse registering it to the corresponding organ mesh Vp.

To quantify distension of the organ within the SOI for each patient, Gaussian curvature and surface normal orientation ($\theta$ and $\phi$) represented in a spherical coordinate system are extracted. The Gaussian curvature at a given point on a surface is a product of principal curvatures of a shape operator.

Embodiments extract a set of tumor specific radiomics $F_R$. The set of tumor specific radiomics $F_R$ may include first order statistics including mean signal intensity, variance and gradient (Sobel and Kirsch gradient operators) to quantify intensity changes. The set of tumor specific radiomics $F_R$ may also include Haralick features computed from the spatial intensity co-occurrence matrices to quantify intensity based tumor heterogeneity. The set of tumor specific radiomics $F_R$ may include Gabor features to quantify signal response at multiple orientations and scales. The set of tumor specific radiomics $F_R$ may include co-occurrence of local anisotropic gradient orientation (CoLlAGe) to quantify gradient based tumor heterogeneity. CoLlAGe features are described in Prasanna, P., Tiwari, P., Madabhushi, A.: *Co-occurrence of local anisotropic gradient orientations (CoLlAGe): A new radiomics descriptor*. Scientific Reports 6 (2016).

Embodiments predict BCR based on a joint probability. Features $F_S$ and $F_R$ from are used to train machine learning classifiers CS and CR using class labels C+ and C−. Class conditional probabilities $p(F_S|\omega_+)$ and $p(F_R|\omega_+)$ are obtained from $C_S$ and $C_R$ respectively, where $\omega_+$ represents occurrence of C+ and $\omega_-$ for C−. Texture characteristics of the tumor captured by FR and organ distension captured by FS are two different classes of features which are assumed to be uncorrelated to each other. Therefore, $p(F_S|\omega_+)$ and $p(F_R|\omega_+)$ can be considered conditionally independent.

$$p(F_S, F_S|\omega_+) = p(F_S|\omega_+)p(F_R|\omega_+) \quad (1)$$

The joint probability $p(F_S, F_S|\omega_+)$ defined above in Eq. 1 represents COnTRa. Formally, COnTRa may be expressed in Bayesian terms as follows:

$$p(\omega_+ | F_S, F_R) = \frac{\prod_{i \in S,R} p(F_i | \omega_+)p(\omega_+)}{\sum_{j \in +,-}\left(\prod_{i \in S,R} p(F_i | \omega_j)p(\omega_j)\right)} = \frac{\prod_{i \in S,R} p(F_i | \omega_+)}{\sum_{j \in +,-}\left(\prod_{i \in S,R} p(F_i | \omega_j)\right)} \quad (2)$$

In this embodiment, we make no assumption of prior probabilities and therefore $p(\omega_+) = p(\omega_-) = 0:5$.

Field effect that is strongly correlated to recurrence and that may mechanically deform prostate capsule surface far beyond the tumor periphery is however not interrogated in conventional recurrence prediction approaches. BCR is often associated with aggressive cancer growth, one that might induce a field effect deformation. Embodiments described herein quantify differential localized deformation of the prostate SOI that arise from the field effect of aggressive growth of the confined tumor for BCR+ patients. Embodiments quantify such localized deformation with deformation magnitude and orientation features to discriminate BCR+ and BCR− patients. Embodiments compute a first probability the region of tissue will experience BCR from the distension features. Embodiments further extract radiomic features from the region of tissue, and compute a second probability that the region of tissue will experience BCR based on the radiomic features. Embodiments then compute a joint probability that the region of tissue will experience BCR based on the first probability and the second probability.

Embodiments extract prostate capsule distension features from pre-treatment MRI images that quantify prostate capsule deformation magnitude and orientation, and predict BCR based on the extracted features. Embodiments identify spatially contextual SOI of the capsule from which the distension features are extracted. Embodiments may train a machine learning classifier with pre-treatment MRI images acquired from a first institution or that were acquired with a first set of imaging parameters, and test the machine learning classifier with a validation or testing set acquired from a different institution or with a second, different set of imaging parameters. The prostate distension features are based on prostate capsule deformation estimated from segmentation of the prostate and are more resilient to scanner and acquisition parameter variability than conventional approaches.

Embodiments predict BCR by creating BCR+ and BCR− cohort atlases, identifying the SOI that significantly differs between the BCR+ and BCR− atlases, and extracting field effect induced organ distension (FOrge) features from the SOI. The FOrge (e.g. distension) features are provided to a machine learning classifier, which computes a first probability that the region of tissue will experience BCR.

In one embodiment, a BCR+ atlas and a BCR− atlas are constructed. An atlas is a representative model of specific characteristics of a given population. A visual anatomic atlas of an organ (e.g., prostate) for a specific class (e.g., BCR+, BCR−) may be generated by registering individual three dimensional (3D) volume meshes to a representative template. A set of pre-treatment images of a region of tissue demonstrating PCa is accessed. Spatially contextual SOI of the prostate capsule are uniquely identified from statistically significant shape differences between BCR+ and BCR− atlases created from the training images. To create subpopulation atlases of each of the groups, prostates inside a given subpopulation (i.e. BCR+ or BCR−) are registered to a representative template. The prostate with median volume for each of the group is selected as the representative template. A segmented mask of the prostate is used to provide anatomical constraint and improve registration accuracy. Registration of the prostate to the representative template is performed in two stages: in a first stage, an initial affine registration is performed followed in a second stage by a non-rigid registration. A block matching strategy is employed to determine the transformation parameters for the affine registration. The affine registration of the moving image to the reference image is followed with a B-spline-based non-rigid registration. The segmented masks of the prostate capsules were given the same transformation as the registered images.

In one embodiment, members of the set of pre-treatment images are first registered (i.e., aligned) to a common canonical frame for statistical comparison. In this example, members of the set of pre-treatment images are T2w prostate MRI images, and alignment of members of the set of pre-treatment images is performed in two stages. In the first stage all, or a threshold number of, prostate MRI images for a given subpopulation (e.g., BCR+ or BCR−) are aligned to the representative template of that group to create a representative atlas of each of the BCR+ and BCR− groups. In the second stage the BCR+ and BCR− atlases are registered to a common space for statistical analysis and comparisons.

Embodiments define a spatially contextual surface of interest from which to compare BCR+ and BCR− prostates. To perform a statistical comparison of the prostate capsule shape between BCR+ and BCR− patients, a BCR+ atlas created for BCR+ patients is registered to a BCR− atlas of the BCR− patients. All, or a threshold number of, the registered prostate capsules, of both the BCR+ and BCR− groups are isotropically scaled with 0.3 mm³ resolution and transformed into a signed distance function. As opposed to the binary representation of a mask where each voxel within the prostate capsule has a value of 1 and a value of 0 outside the capsule, the value assigned to each voxel is determined based on the distance of a given voxel from the capsule boundary. Consequently, the signed distance function yields positive values for voxels inside the prostate capsule, while the value of the voxel decreases as it approaches the boundary where the signed distance function is zero, becomes negative outside the prostate capsule, and continues to decrease depending on the distance of the voxel from the prostate capsule.

The signed distance representation gives an implicit representation of the prostate boundary and aids in a t-test based comparison of the shape in a non-parametric General Linear Model (GLM) based t-test framework. Statistically significant shape differences are quantified with 5000 random permutation testing with the p-value being corrected for multiple comparison. A voxel is considered as belonging to a region exhibiting statistically significant differences between shapes for BCR+ and BCR− patients if the p-value estimated by this testing is less than 0.05. Significant shape differences between BCR+ and BCR− cohorts are then quantified as SOI.

Figure 2:
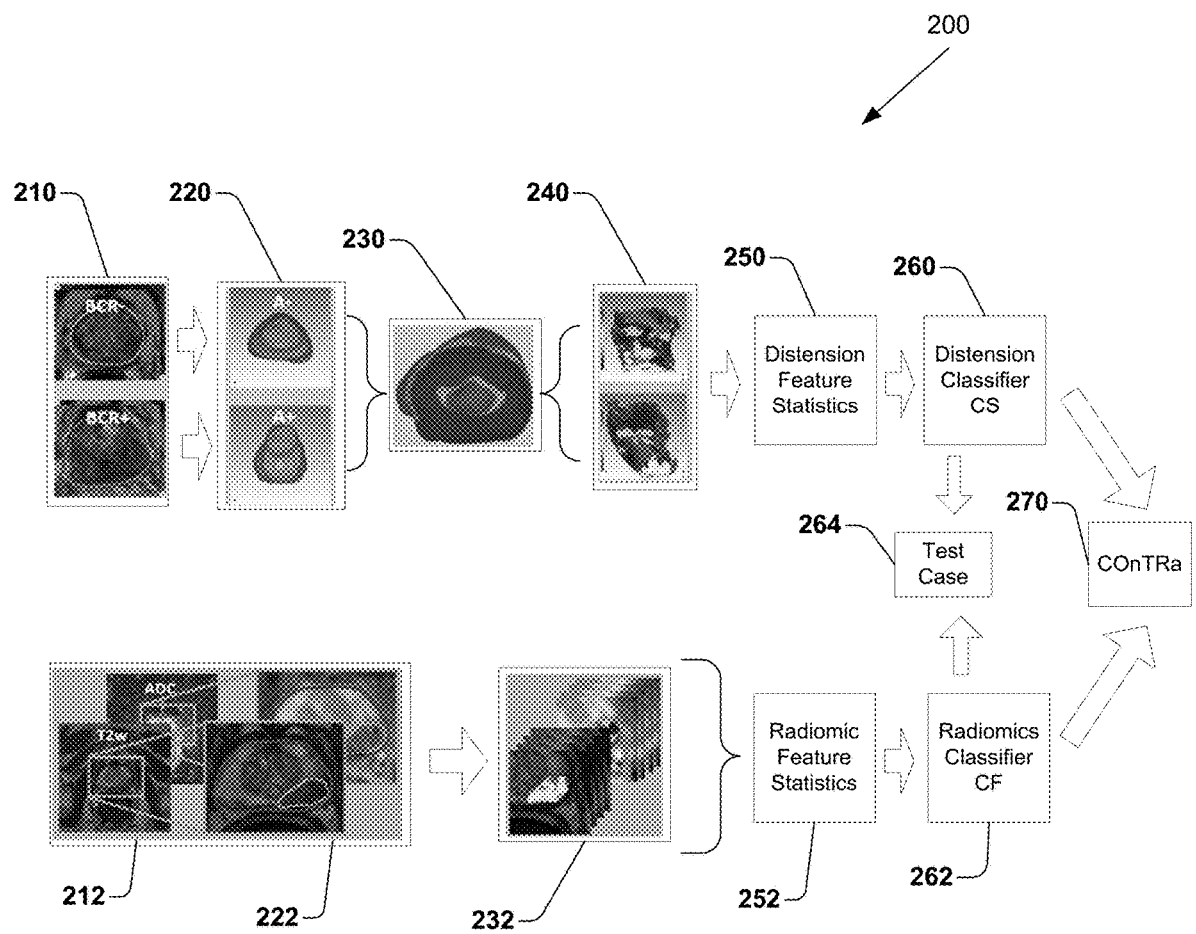
FIG. 2 is a schematic overview of an exemplary workflow for biochemical recurrence (BCR) prediction.

FIG. 2 illustrates an example embodiment of a COnTRa framework 200 for quantifying statistical shape differences and predicting PCa BCR as described above. FIG. 2 includes, at 210, accessing a set of T2w MRI imagery of BCR+ and BCR− prostates. The prostates may be segmented from the background of the image using automated segmentation techniques. At 220, the T2w MRI imagery of BCR+ and BCR− prostates is used to construct A− (e.g., BCR−) and A+ (e.g., BCR+) atlases. An SOI is defined, based on the A− and A+ atlases at 230. Distension features (e.g., shape features, FOrge features) are extracted at 240, and distension feature statistics are computed at 250. The distension features and distension feature statistics are used to train a machine learning classifier $C_s$ at 260. The machine learning classifier $C_s$ may then be used to compute a first probability that a region of tissue demonstrating PCa will experience BCR. This probability is provided to a COnTRa component (e.g., circuit, processor, apparatus) at 270.

FIG. 2 also includes, at 212 accessing a set of MRI ADC DCE sequences of BCR+ and BCR− prostates. A region of interest may be segmented at 222, and radiomic features extracted from the region of interest at 232. At 252, radiomic feature statistics are computed from the radiomic features. The radiomic features are provided to a second machine learning classifier $C_R$ at 262. The machine learning classifier $C_R$ may then be used to compute a second probability that a region of tissue demonstrating PCa will experience BCR based on the radiomic features or statistics. This probability is provided to a COnTRa component at 270. The COnTRa component then computes a joint probability that the region of tissue will experience BCR based on the first probability and the second probability. In one embodiment, the machine learning classifier $C_R$ and machine learning classifier $C_S$ are trained and tested on a validation or test set of images at 264.

Figure 4:
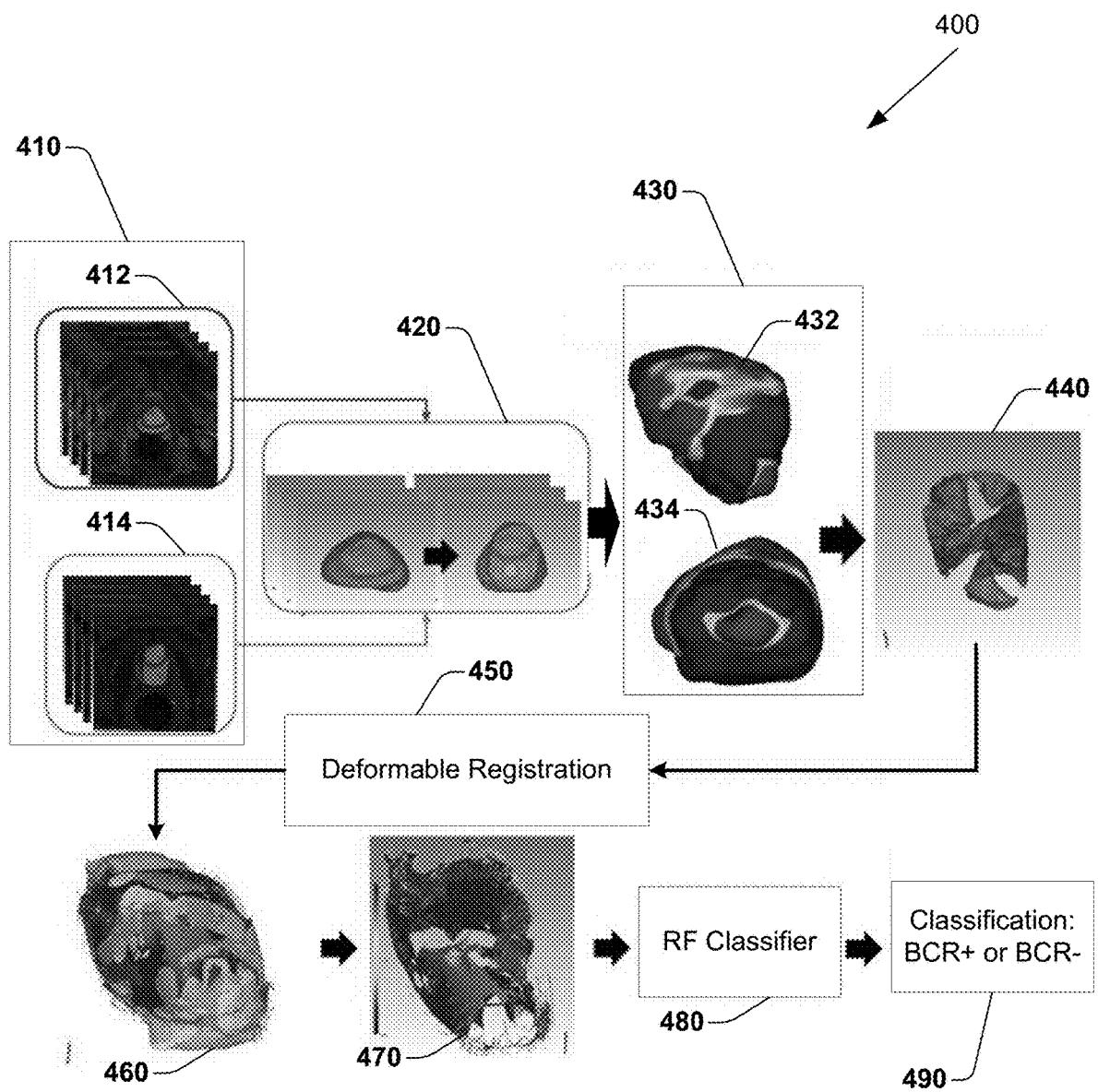
FIG. 4 is a schematic overview of an exemplary workflow for BCR prediction.

FIG. 4 is a schematic overview of an example workflow 400 for quantifying statistical shape differences between BCR+ and BCR− prostates that provides more details than illustrated in FIG. 2. Workflow 400 may be employed by embodiments described herein. FIG. 4 illustrates, at 410, a set of registered BCR+ prostate capsule masks 412, and a set of registered BCR− prostate capsule masks 414. At 420, a generalized linear model based T-test is applied to the set of registered BCR+ prostate capsule masks 412 and the set of registered BCR− prostate capsule masks 414 to identify shape differences. At 430, statistically significant differences in the shape of the prostate capsules are computed. A sagittal view 432 and an axial view 434 of a prostate capsule are illustrated. At 440, an SOI that is significantly different between the BCR+ and the BCR− cohorts is identified. At 450, the SOI is deformably registered to a prostate capsule that is being analyzed. An image of the SOI overlaid on the prostate capsule being analyzed is illustrated at 460. A set of curvature and surface normal features are extracted from the SOI at 470. The set of curvature and surface normal features are provided to a machine learning classifier, in this example a random forest classifier, at 480. The random forest classifier computes a probability that the prostate capsule will experience BCR, and at 490, a classification of the prostate capsule as likely to experience BCR or unlikely to experience BCR is produced.

Embodiments quantify the irregular deformation of the prostate capsule by extracting, from the SOI, curvature magnitude and surface normal orientation features. The surface curvature and orientation features are however more meaningful in the spatially contextual SOI which is significantly different between the BCR+ and BCR− cohorts, than in similar features extracted over the entire surface of the prostate capsule. To extract the curvature and surface orientation features from spatially contextual SOI, patient images are rigidly registered to the BCR− template selected for statistical comparison of BCR+ and BCR− cohorts. The SOI mask identified via population based statistical comparison is then registered to patient mask using a B− spline based registration. This ensures that a patient mask is not deformed and remains unaffected. The registered mask is then considered as an SOI for conversion to an SOI mesh, and for feature extraction.

The SOI mask for the new patient is then converted to a SOI mesh. An SOI mesh includes a plurality of vertices. The surface normal orientation provides the direction of the surface deformation and surface Gaussian and mean curvature provides the magnitude of the deformation. Curvature and normal orientation features are extracted for vertices of the mesh.

In one embodiment, the surface normal orientation provides the direction of the surface deformation and surface Gaussian curvature provides the magnitude. Gaussian curvature and normal orientation features are extracted for vertices of the mesh. Kth Gaussian curvature discretized at vertex v is given by:

$$K_v = 2 \times PI - \sum_{\nabla} (v_\gamma)$$

where $\Sigma_\nabla$ is the summation of all facets and $v_\gamma$ is the orientation at v. For a vertex the normal orientation is represented in a spherical coordinate system and θ (the angle between the projection of the normal vector in XY plane and X axis) and φ (the angle between the projection of the normal vector in Y Z plane and Z axis) are extracted.

In one embodiment, for every patient three arrays of curvature, and θ and φ are created and statistical measures including mean, standard deviation, inter-quartile range (Q1 and Q3), range, skewness and kurtosis are extracted. Thus, in this example, the dimension of the feature vector for every patient is 21, where the feature vector is derived from three features (curvature, θ and φ) and seven statistical measures (mean, standard deviation, inter-quartile range (Q1 and Q3), range, skewness and kurtosis) for each of the three features.

In another embodiment, for every patient four arrays, Gaussian curvature, mean curvature, θ and φ (3d orientation in spherical coordinate system) are created and statistical measures like mean, standard deviation, inter-quartile range (Q1 and Q3), range, skewness and kurtosis are extracted. Thus, in this example, the dimension of the feature vector for every patient is 28, derived from four features (Gaussian curvature, mean curvature, θ and φ) and seven statistical measures (mean, standard deviation, inter-quartile range (Q1 and Q3), range, skewness and kurtosis) for each of the four features. A non-parametric Gini importance based feature selection technique is used to select the most discriminative features. Gaussian curvature and normal orientation do not follow a normal distribution. Thus, conventional feature selection strategies are not effective in selecting discriminative features that are based on Gaussian curvature and normal orientation. In another embodiment, other techniques for selecting discriminative features may be employed.

Figure 3:
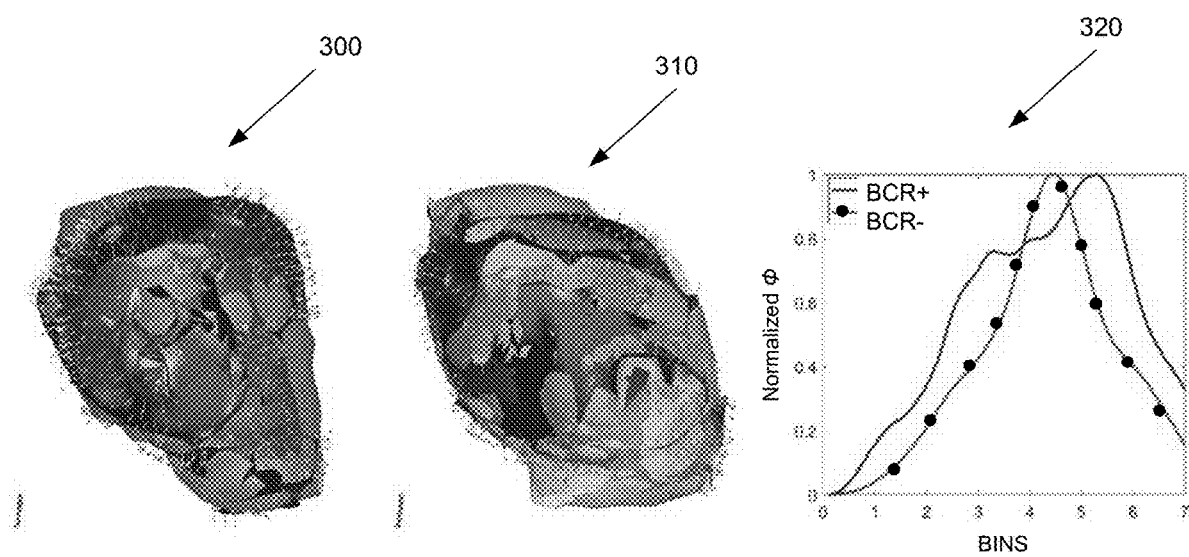
FIG. 3 illustrates a surface of interest (SOI) overlaid on a prostate capsule.

FIG. 3 illustrates, at 300, an example SOI mask overlaid on a BCR+ prostate capsule. FIG. 3 also illustrates, at 310, the SOI mask overlaid on a BCR− prostate capsule. FIG. 3 further illustrates a graph 320 of the differential distribution of φ (the angle between the projection of the normal vector in the Y Z plane and Z axis) between the BCR+ SOI and the BCR– SOI. The x-axis of graph 320 indicates the number of bins, and the y-axis indicates the normalized ϕ.

Example methods and apparatus demonstrably improve on conventional technologies for predicting BCR. For example, embodiments described herein predict BCR with an average area under the curve (AUC) of at least 0.84 and with an accuracy of at least 76.7%, compared to radiomics alone (66.7%) and shape alone (63.3%) techniques. Additionally, conventional approaches that employ clinical variables such as PSA, Gleason, and PIRADS-v2 to construct a linear discriminant analysis (LDA) classifier trained on the same training set as embodiments described herein, achieve an AUC of only 0.57.

By increasing the accuracy with which BCR is predicted, example methods and apparatus produce the concrete, real-world technical effect of increasing the probability that at-risk patients receive timely treatment tailored to the particular pathology they exhibit. The additional technical effect of reducing the expenditure of resources and time on patients who have a less aggressive pathology is also achieved. Example embodiments further improve on conventional approaches by providing a more accurate second reader to facilitate the reduction of inter-reader and intra-reader variability among human radiologists or oncologists. Example methods and apparatus thus improve on conventional methods in a measurable, clinically significant way. When implemented as part of a personalized medicine system, a computer assisted diagnostic (CADx) system, or a BCR prediction system which may include a computer or a processor configured to predict BCR, example embodiments improve the performance of a machine, computer, or computer-related technology by providing a more accurate and more reliable prediction of disease recurrence compared to conventional approaches to controlling a machine to predict disease recurrence.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 5:
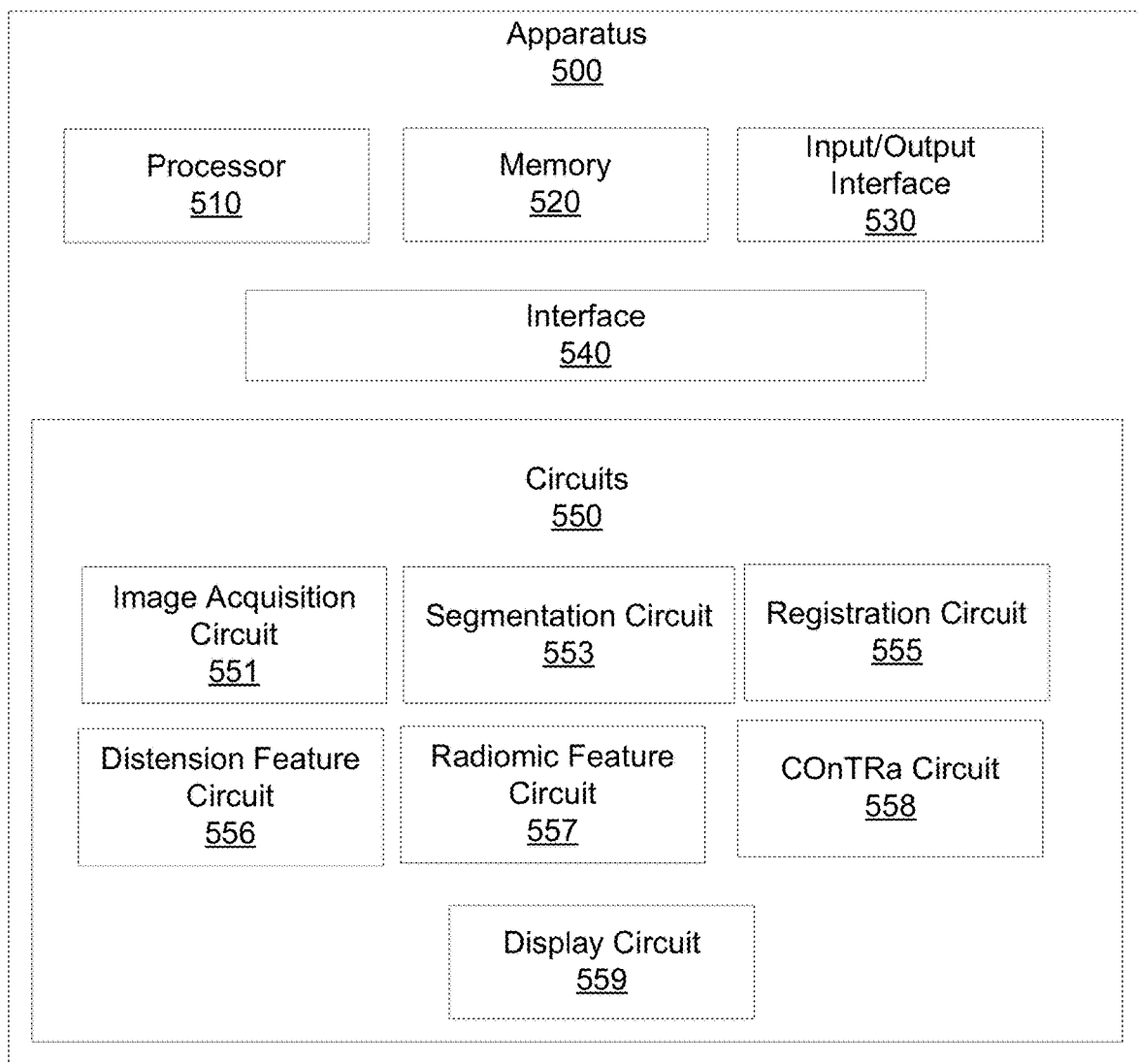
FIG. 5 illustrates an example apparatus for predicting BCR.

FIG. 5 illustrates an example apparatus 500 that predicts prostate cancer BCR. Apparatus 500 includes a processor 510. Apparatus 500 also includes a memory 520. Processor 510 may, in one embodiment, include circuitry such as, but not limited to, one or more single-core or multi-core processors. Processor 510 may include any combination of general-purpose processors and dedicated processors (e.g., graphics processors, application processors, etc.). The processors may be coupled with or may include memory (e.g. memory 520) or storage and may be configured to execute instructions stored in the memory or storage to enable various apparatus, applications, or operating systems to perform the operations. Memory 520 is configured to store a digitized image of a region of tissue demonstrating cancerous pathology.

In one embodiment, memory 520 is configured to store a first pre-treatment image of a region of tissue demonstrating PCa, and a second pre-treatment image of the region of tissue, a recurrence-negative (e.g., C–, BCR–) median template, and a surface of interest (SOI) mask. The SOI mask is a spatially contextual surface of interest that defines a region of differential distension between recurrence-positive (e.g., C+, BCR+) and recurrence negative (e.g. C–, BCR–) regions of tissue. The region of tissue represented in the first pre-treatment image and the second pre-treatment image includes a prostate capsule. The first pre-treatment image and the second pre-treatment image each have a plurality of voxels, a voxel having an intensity. Apparatus 500 also includes an input/output (I/O) interface 530. Apparatus 500 also includes a set of circuits 550. The set of circuits 550 includes an image acquisition circuit 551, a segmentation circuit 553, a registration circuit 555, a distension feature circuit 556, a radiomic feature circuit 557, a COnTRa circuit 558, and a display circuit 559. Apparatus 500 further includes an interface 540 that connects the processor 510, the memory 520, the I/O interface 530, and the set of circuits 550.

Image acquisition circuit 551 is configured to access the first pre-treatment image and the second pre-treatment image. The first pre-treatment image and the second pre-treatment image may be pre-treatment images of a region of tissue demonstrating PCa. The first pre-treatment image and the second pre-treatment image each include a plurality of voxels, a voxel having an intensity. Accessing the first pre-treatment image and the second pre-treatment image includes acquiring electronic data, reading from a computer file, receiving a computer file, reading from a computer memory, or other computerized activity. In another embodiment, accessing the first pre-treatment image and the second pre-treatment image may include accessing a network attached storage (NAS), a cloud storage system, or other type of electronic storage system. Accessing the first pre-treatment image and the second pre-treatment image may, in one embodiment, include accessing a NAS device, a cloud storage system, or other type of electronic storage system using input/output interface 530. In one embodiment, the first pre-treatment image or the second pre-treatment image is a T1W MRI image, or a T2W MRI image. In one embodiment, the second pre-treatment image is a T2W apparent diffusion coefficient (ADC) dynamic contrast enhanced (DCE) MRI image of the region of tissue. In another embodiment, other imaging modalities, approaches, or parameters may be used to generate and access the image accessed by image acquisition circuit 551.

In one embodiment, image acquisition circuit 551 is configured to pre-process the first pre-treatment image or the second pre-treatment image. Pre-processing the first pre-treatment image or the second pre-treatment image may include applying N4 bias field correction to the first pre-treatment image or the second pre-treatment image to reduce magnetic bias. In another embodiment, other pre-processing techniques may be employed.

Segmentation circuit 553 is configured to generate a first segmented prostate by segmenting a prostate capsule represented in the first pre-treatment image. Segmentation circuit 553 is also configured to generate a second segmented prostate by segmenting the prostate capsule represented in the second pre-treatment image. In one embodiment, segmentation circuit 553 is configured to segment the prostate capsule using a statistical shape and appearance model-based segmentation technique. In another embodiment, segmentation circuit 553 may be configured to use other segmentation techniques.

Registration circuit 555 is configured to generate a registered prostate by registering the first segmented prostate with the SOI mask. Registration circuit 555 is also configured to generate a patient-specific SOI mask from the registered prostate and the SOI mask. In one embodiment, registration circuit 555 is configured to register the SOI mask with the first pre-treatment image using an affine registration technique and a B-spline registration technique. Registration circuit 555 is further configured to generate a patient-specific SOI mesh from the patient-specific SOI mask. The patient-specific mesh includes a plurality of vertices.

In one embodiment, registration circuit 555 is configured to generate a registered prostate by registering the segmented prostate with the BCR− median template. The BCR− median template is the image of the prostate with median volume for the BCR− group used to generate a BCR− atlas. Registration circuit 555 is further configured to generate a registered SOI mask by registering the SOI mask with the registered prostate. In one embodiment, registration circuit 555 is configured to register the segmented prostate with the BCR− median template using a rigid registration technique. In one embodiment, registration circuit is 555 configured to register the SOI mask with the registered prostate using a B-spline registration technique. In one embodiment, registration circuit 555 is configured to employ an affine registration technique. In this embodiment, a block matching strategy is employed to determine the transformation parameters for the affine registration.

In one embodiment, registration circuit 555 is configured to generate a patient-specific SOI mask from the registered prostate and the registered SOI mask. The patient-specific SOI mask defines a surface area of the prostate capsule represented in the first pre-treatment image that corresponds with the SOI mask identified as having statistically significant shape differences between members of a BCR+ atlas and a BCR− atlas. Registration circuit 555 is further configured to generate a patient-specific SOI mesh from the patient-specific SOI mask. The patient-specific SOI mesh includes a plurality of vertices from which distension (e.g., shape, FOrge) features may be extracted.

Distension feature circuit 556 is configured to extract a set of distension features from the patient-specific SOI mesh. Distension feature circuit 556 is further configured to compute a first probability of PCa recurrence based on the set of distension features. The set of distension features includes a Gaussian curvature ($\theta$) feature, and a surface normal orientation ($\Phi$) feature represented in a spherical coordinate system. The set of distension features also includes a $\theta$ kurtosis feature, a $\Phi$ skewness feature, a $\Phi$ standard deviation feature, and a $\Phi$ mean feature computed from the $\theta$ feature and the $\Phi$ feature. Distension circuit 556 further comprises a shape machine learning component configured to compute the first probability based on the set of distension features. In one embodiment, the shape machine learning component is configured as a random forest (RF) classifier having a depth of two and 1000 trees.

In one embodiment, distension feature circuit 556 is configured to extract a set of FOrge features from the patient-specific SOI mesh. In this embodiment, distension feature circuit 556 is further configured to compute a probability that the region of tissue will experience BCR based, at least in part, on the set of FOrge features. In one embodiment, the set of FOrge features includes a curvature magnitude feature, an XY plane surface normal orientation feature, and an XZ plane surface normal orientation feature. In this embodiment, the set of FOrge features further includes a curvature magnitude standard deviation feature, a curvature magnitude range feature, a curvature magnitude mean feature, an XY plane surface normal orientation mean feature, an XY plane surface normal orientation kurtosis feature, an XY plane surface normal orientation range feature, an XY plane surface normal orientation standard deviation feature, an XZ plane surface normal orientation standard deviation feature, and an XZ plane surface normal orientation range feature. In another embodiment, the set of FOrge features may include other, different features.

In one embodiment, distension feature circuit 556 includes a shape machine learning component configured to compute the probability based on the set of FOrge features. In this embodiment, the shape machine learning component is configured as an RF classifier having a depth of two, and 10000 trees. In another embodiment, the shape machine learning component may be configured as an RF classifier with other, different parameters. In another embodiment, the shape machine learning component may be another different type of machine learning classifier, including a support vector machine (SVM), a linear discriminant analysis (LDA) classifier, a quadratic discriminant analysis (QDA) classifier, a convolutional neural network (CNN), or other type of machine learning or deep learning classifier.

Radiomic feature circuit 557 is configured to extract a set of radiomics features from the second pre-treatment image. Radiomic feature circuit 557 is also configured to compute a second probability of PCa recurrence based on the set of radiomics feature. The set of radiomics features includes a subset of first order statistical features, a subset of Haralick features, a subset of Gabor features, and a subset of co-occurrence of local anisotropic gradient orientation (CoLlAGe) features. The subset of first order statistics quantifies intensity changes, and may include a mean signal intensity feature, a variance and gradient feature (e.g., Sobel and Kirsh gradient operators). The subset of Haralick features may be computed from spatial intensity co-occurrence matrices based on the second pre-treatment image, and quantifies intensity-based tumor heterogeneity. The subset of Gabor features quantifies signal response at multiple orientation and angles. The subset of CoLlAGe features quantifies gradient based tumor heterogeneity. CoLlAGe involves assigning an image voxel an entropy value associated with the co-occurrence matrix of gradient orientations computed around a voxel.

Radiomic feature circuit 557 further comprises a radiomics machine learning component configured to compute the second probability based on the set of radiomics features. The radiomics machine learning component is configured as a random forest (RF) classifier having a depth of two and 1000 trees. In another embodiment, the radiomics machine learning component may be another different type of machine learning classifier, including a support vector machine (SVM), a linear discriminant analysis (LDA) classifier, a quadratic discriminant analysis (QDA) classifier, a convolutional neural network (CNN), or other type of machine learning or deep learning classifier.

COnTRa circuit 558 is configured to compute a joint probability that the region of tissue will experience PCa recurrence. COnTRa circuit 558 computes the joint probability based on the first probability and the second probability. COnTRa circuit 558 may be configured to compute the joint probability as $p(F_S, F_S | \omega_+)$ as defined above in Eq. 1. COnTRa circuit 558 may compute the joint probability in Bayesian terms as defined in Eq. 2 above.

In one embodiment, COnTRa circuit 558 is further configured to classify the region of tissue as likely to experience BCR or unlikely to experience BCR based, at least in part, on the joint probability. In one embodiment, COnTRa circuit 558 computes the probability based, at least in part, on the joint probability and at least one of: the set of distension features, the set of FOrge features, the set of radiomics features, the patient-specific SOI mask, the patient-specific SOI mesh, or the image. In one embodiment, COnTRa circuit 558 is further configured with a classification machine learning component. For example, COnTRa circuit 558 may be configured with a classification machine learning component configured as a linear discriminant analysis (LDA) classifier, a quadratic discriminant analysis (QDA) classifier, a support vector machine (SVM) classifier, or a random forest (RF) classifier.

Display circuit 559 is configured to display the joint probability. In one embodiment, display circuit 559 is configured to display the classification, the joint probability, the set of distension features, the set of radiomic features, the set of FOrge features, a cancer treatment plan, the patient-specific SOI mask, the patient specific SOI mesh, or the first pre-treatment image or the second pre-treatment image on a computer monitor, a smartphone display, a tablet display, or other displays. Displaying the classification, the joint probability, the set of distension features, the set of radiomic features, the set of FOrge features, a cancer treatment plan, the patient-specific SOI mask, or the first pre-treatment image or the second pre-treatment image may also include printing the classification, the joint probability, the set of distension features, the set of radiomic features, the set of FOrge features, a cancer treatment plan, the patient-specific SOI mask, or the first pre-treatment image or the second pre-treatment image. Display circuit 5559 may also control a CADx system, a monitor, or other display, to display operating parameters or characteristics of distension circuit 556, radiomic feature circuit 557, or COnTRa circuit 558, including a machine learning classifier, during both training and testing, and during clinical operation.

Embodiments described herein, including apparatus 500, resolve features extracted from the first pre-treatment image or the second pre-treatment image at a higher order or higher level than a human can resolve in the human mind or with pencil and paper. For example, the curvature magnitude feature, the XY plane surface normal orientation feature, and the XZ plane surface normal orientation feature are not biological properties of cancerous tissue that a human eye can perceive. A human prostate does not include an overlaid SOI mesh, and an SOI mesh cannot be stored in a human mind. The set of distension features provided to the machine learning classifier is of a different nature than the prostate capsule represented in the image, or the patient-specific SOI mask. The joint probability computed by COnTRa circuit 558 is of a fundamentally different nature than the first pre-treatment image or the second pre-treatment image or the radio frequency signal acquired from the region of tissue to generate the MRI image.

Figure 6:
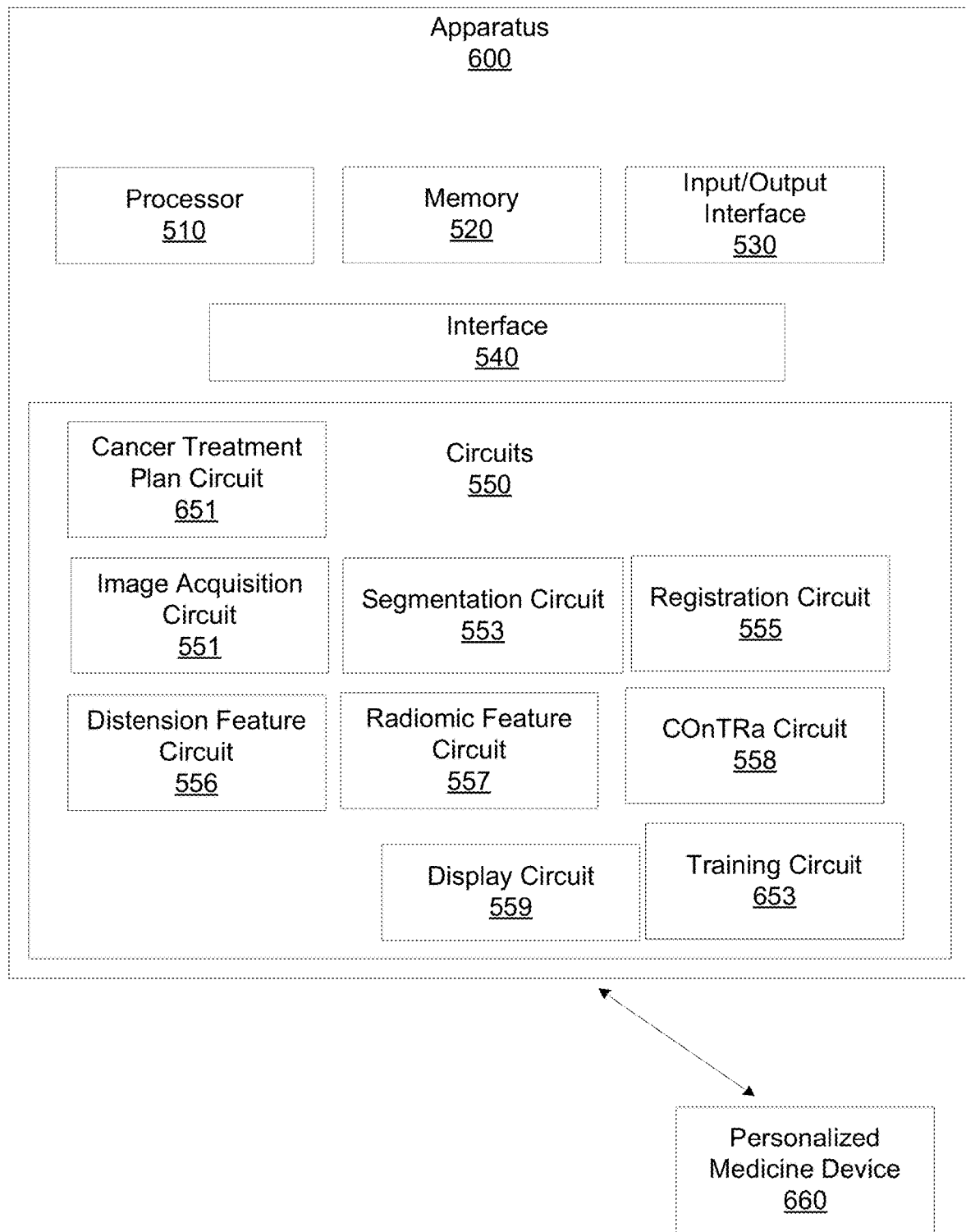
FIG. 6 illustrates an example apparatus for predicting BCR.

FIG. 6 illustrates an example apparatus 600 that is similar to apparatus 500 but that includes additional details and elements. In one embodiment of apparatus 600, the set of circuits 550 further includes a cancer treatment plan circuit 655. Cancer treatment plan circuit 655 is configured to generate a cancer treatment plan for the patient of which the first pre-treatment image or the second pre-treatment image was acquired based, at least in part, the joint probability and at least one of the first probability, the second probability, the set of distension features, the set of radiomic features, the set of FOrge features, the patient-specific SOI mask, or the first pre-treatment image or the second pre-treatment image. Defining a personalized cancer treatment plan facilitates delivering a particular treatment that will be therapeutically active to the patient, while minimizing negative or adverse effects experienced by the patient. For example, the cancer treatment plan may suggest a surgical treatment, may define an immunotherapy agent dosage or schedule, or a chemotherapy agent dosage or schedule, for a patient identified as likely to experience BCR. For a patient classified as unlikely to experience BCR, other treatments may be suggested.

In another embodiment, apparatus 600 may control a CADx system to classify the region of tissue represented in the first pre-treatment image or the second pre-treatment image based, at least in part, on the joint probability. In other embodiments, other types of CADx systems may be controlled, including CADx systems for predicting recurrence or progression in other tissue presenting other, different pathologies that may be distinguished based on combined distension and radiomic features. For example, embodiments described herein may be employed to predict disease progression or recurrence based on probabilities computed from combined distension and radiomic features by a machine learning classifier in breast cancer (BCa), kidney disease, lung cancer, or brain pathologies.

In another embodiment of apparatus 600, the set of circuits 550 further includes a training circuit 653 configured to train distension feature circuit 556 or radiomic feature circuit 557. Training distension feature circuit 556 or radiomic feature circuit 557 may include training a machine learning classifier, including the first machine learning classifier or the second machine learning classifier. In one embodiment, training circuit 653 is configured to access a dataset of digitized images of a region of tissue demonstrating PCa. The dataset of digitized images includes, in this example, pre-treatment T1W MRI images, or pre-treatment T2W MRI images. In one embodiment, training circuit 653 is configured to control image acquisition circuit 551 to access the dataset of digitized images of a region of tissue demonstrating PCa.

In one embodiment, training the first machine learning classifier includes generating a BCR+ atlas, and a BCR− atlas. In this embodiment, training circuit 653 is configured to generate the BCR+ atlas and the BCR-atlas by accessing a set of pre-treatment images of a region of tissue demonstrating PCa. Accessing the set of pre-treatment images includes acquiring electronic data, reading from a computer file, receiving a computer file, reading from a computer memory, or other computerized activity. The set of pre-treatment images includes a plurality of BCR+ images and a plurality of BCR− images. Training circuit 653 is also configured to generate a pre-processed set by pre-processing the set of pre-treatment images using N4 bias field correction to reduce magnetic bias.

Training circuit 653 is also configured to select a BCR+ subset from the pre-processed set. Training circuit 653 is also configured to select a BCR− subset from the pre-processed set. In one example embodiment, generating a BCR+ atlas and a BCR− atlas may include selecting MRI images of prostates from a prostate MRI registry of at least 874 patients. Availability of complete image datasets (including T1w, T2w and ADC maps), absence of treatment for PCa before MRI, presence of clinically localized PCa, Gleason score available from pretreatment biopsy and/or from radical prostatectomy specimens, and post-treatment outcome data including post-treatment PSA and a minimum of 3 years of follow-up may be used as inclusion criteria for selection into the BCR+ subset or the BCR− subset. In this example, of the 874 patients in the registry, 80 cases met these inclusion criteria. BCR+ and BCR− cases for atlas creation are selected from these 80 patients. To reduce statistical biases of the atlases, equal number of patients in BCR+ and BCR− cohorts (25 each); similar Gleason scores (6 to 9); and similar tumor stages (T2 to T3) are used to identify, in this example, 50 patients. The remaining 30 patients out of 80 are used for validation. The BCR+ patients had a mean recurrence time of 18.5 months. The BCR− patients had a mean follow-up time of 4.2 years. In another embodiment, other parameters may be employed to select subsets and generate the atlases.

Training circuit 653 is also configured to segment a prostate capsule represented in a member of the BCR+ subset. Training circuit 653 is also configured to segment a prostate capsule represented in a member of the BCR− subset. In one embodiment, training circuit 653 is configured to automatically segment a the prostate capsule represented in a member of the BCR+ subset or the BCR− subset using a statistical shape and appearance model. In one embodiment, a shape and appearance model of a prostate is created from a manual segmentation of the prostate. A training set of segmented prostates may be generated. Given an un-segmented prostate, the statistical shape and appearance model automatically segments the prostate by minimizing appearance/intensity differences between the created model and the un-segmented prostate constrained by the statistical shape of the prostate learned from a training set. In one embodiment, training circuit 653 is configured to control segmentation circuit 653 to segment a prostate capsule represented in a member of the BCR+ subset and to segment a prostate capsule represented in a member of the BCR− subset.

Training circuit 653 is also configured to select a BCR+ median image from the BCR+ subset. Training circuit 653 is also configured to select a BCR− median image from the BCR− subset. Selecting the BCR+ median image or the BCR− median image includes selecting the image of the prostate with median volume for the BCR+ subset or the BCR− subset.

Training circuit 653 is also configured to generate a BCR+ atlas by registering a member of the BCR+ subset to the BCR+ median image. Training circuit 653 is further configured to generate a BCR− atlas by registering a member of the BCR− subset to the BCR− median image.

The BCR+ atlas and the BCR− atlas are employed by embodiments described herein to perform a statistical comparison of the prostate capsule shape between BCR+ and BCR− patients. To perform a statistical comparison of the prostate capsule shape between BCR+ and BCR− patients, embodiments described herein register the BCR+ atlas images to the BCR− atlas images. In one embodiment, a threshold number (e.g., 100%, 90%, 75%) of registered prostate capsules of both the BCR+ and BCR− groups are isotropically scaled with 0.3 $mm^3$ resolution and transformed into a signed distance function. As opposed to the binary representation of a mask where each voxel within the prostate capsule has a value of 1 and a value of 0 outside the capsule, the value assigned to each voxel is determined by embodiments described herein based on the distance of a given voxel from the capsule boundary. Consequently, the signed distance function yields positive values for voxels inside the prostate capsule, while the value of the voxel decreases as it approaches the boundary where the signed distance function is zero, becomes negative outside the prostate capsule, and continues to decrease depending on the distance of the voxel from the prostate capsule.

The signed distance representation gives an implicit representation of the prostate boundary and aids in a t-test based comparison of the shape in a non-parametric General Linear Model (GLM) based t-test framework. Statistically significant shape differences are quantified with random permutation testing with the p-value being corrected for multiple comparisons. A voxel is considered as belonging to a region exhibiting statistically significant differences between shapes for BCR+ and BCR− patients if the p-value estimated by this testing is less than 0.05. Voxels of the prostate surface demonstrating significant shape differences between BCR+ and BCR− cohorts are then quantified as the SOI.

The population based statistics used to identify spatially contextual SOI that significantly differs between the two cohorts is, however, dependent on the quality of the registration of the atlases. Thus, embodiments may consider registration accuracy presented in terms of Dice similarity coefficient (DSC) and mean absolute surface distance (MASD). In one embodiment, the DSC of the BCR+ atlas is at least 0.98+−0.01 and that of the BCR− atlas is at least 0.97+−0.01. In this example, the MASD of the BCR+ atlas is at least 0.30+−0.11 mm and that of the BCR− atlas is at least 0.40+−0.14 mm. Embodiments facilitate ensuring atlas registration accuracy sufficient for statistical shape comparison that results in BCR prediction accuracy that is greater than conventional approaches. In another embodiment, other parameters may be employed to ensure the registration accuracy of the atlases.

In one embodiment, the set of circuits 550 further includes an atlas circuit 651. Atlas circuit 651 is configured to generate a C+ atlas (e.g., a BCR+ atlas) and generate a C− atlas (e.g., BCR− atlas). Atlas circuit 651 is further configured to generate a registered atlas by registering the C+ atlas with the C− atlas. Atlas circuit 651 is further configured to generate the SOI mask from the registered atlas.

FIG. 6 also illustrates a personalized medicine device 660. Personalized medicine device 660 may be, for example, a CADx system, a prostate cancer BCR prediction system, or other type of personalized medicine device that may be used to facilitate the prediction of cancer progression or recurrence. In one embodiment, the cancer treatment plan circuit 651 may control personalized medicine device 660 to display the joint probability, the set of distension features, the set of radiomics features, the set of FOrge features, the cancer treatment plan, or the pre-treatment images on a computer monitor, a smartphone display, a tablet display, or other displays.

Displaying the joint probability, the set of distension features, the set of radiomics features, the set of FOrge features, the cancer treatment plan, or the pre-treatment images involves but is not limited to extracting and changing the character of information present in a region of tissue (e.g. biological tissue), to a radiological image (e.g. MRI image), to changing the information present in the image to information of a different character in the set of distension or radiomics features, the joint probability, and the cancer treatment plan. Embodiments described herein further transform the character of information to information suitable for display on, for example, a computer monitor, a smartphone display, a tablet display, or other displays. Thus, embodiments described herein use a combined order of specific rules, elements, or components that render information into a specific format that is then used and applied to create desired results more accurately and with greater reliability than conventional approaches.

Figure 7:
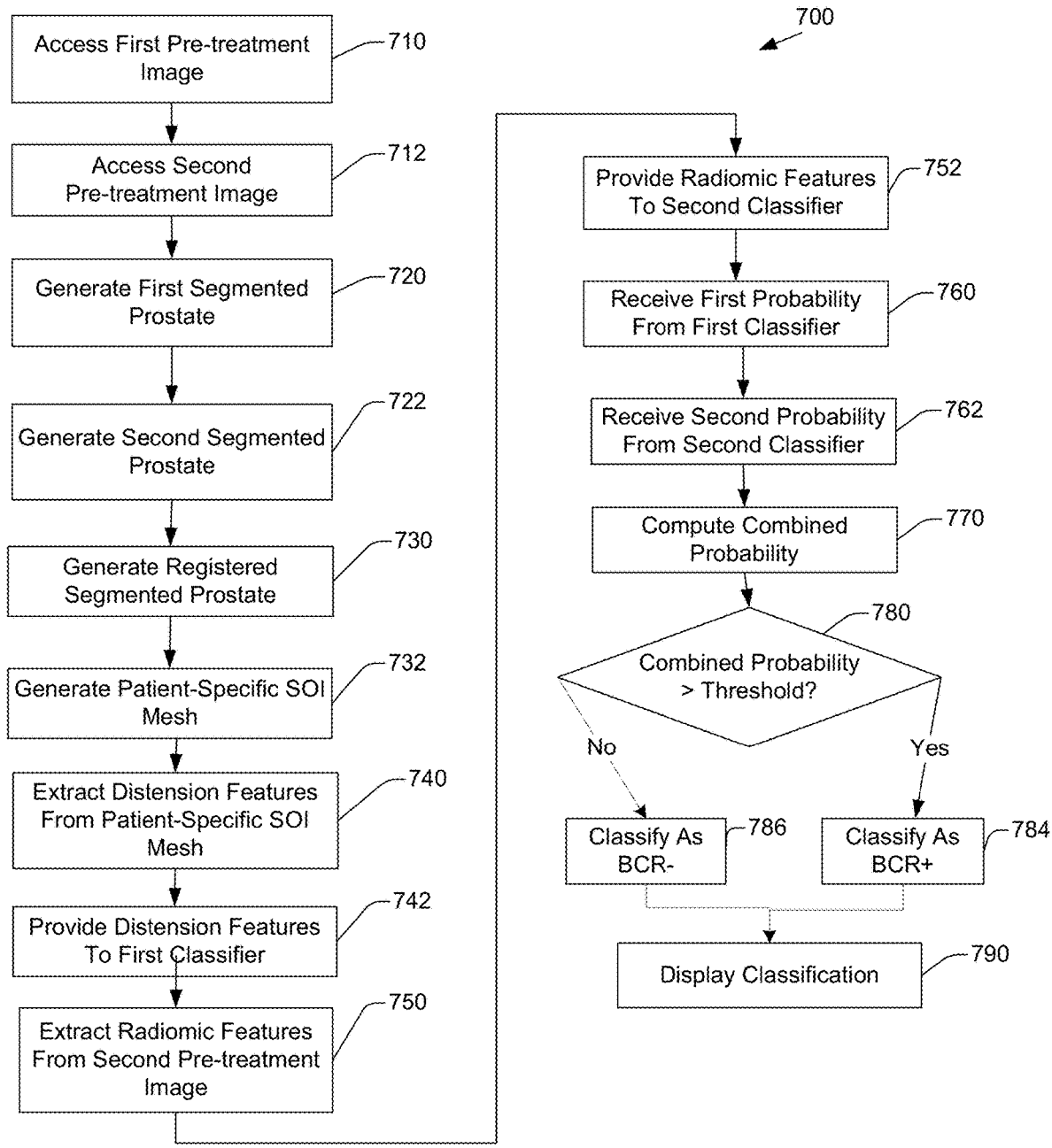
FIG. 7 illustrates an example method for predicting BCR.

FIG. 7 illustrates a computerized method 700 for predicting prostate cancer (PCa) recurrence. Method 700 may, in one embodiment, be implemented by apparatus 500 or apparatus 600. Method 700 includes, at 710 accessing a first pre-treatment radiological image of a region of tissue demonstrating PCa. Method 700 also includes, at 712 accessing a second pre-treatment radiological image of the region of tissue. In this embodiment, the first pre-treatment radiological image is a T2w MRI image. In one embodiment, the second pre-treatment radiological image is a T2w apparent diffusion coefficient (ADC) dynamic contrast enhanced (DCE) magnetic resonance imaging (MRI) image of the region of tissue. Accessing the first pre-treatment radiological image or the second pre-treatment radiological image includes acquiring electronic data, reading from a computer file, receiving a computer file, reading from a computer memory, or other computerized activity. In other embodiments, the first pre-treatment radiological image or the second pre-treatment radiological image may be of other, different types of tissue demonstrating other, different pathologies imaged using different imaging techniques or parameters. For example, in one embodiment, the first pre-treatment radiological image or the second pre-treatment radiological image may be an MRI image of a different region of tissue demonstrating cancerous pathology in which field effect induced organ distension is predictive of biochemical recurrence. In another embodiment, the image is a computerized tomography (CT) image of region of tissue demonstrating cancerous pathology Method 700 also includes, at 720, generating a first segmented prostate by automatically segmenting a prostate capsule represented in the first pre-treatment radiological image. Method 700 also includes, at 722, generating a second segmented prostate by automatically segmenting the prostate capsule represented in the second pre-treatment radiological image.

Method 700 also includes, at 730, generating a registered segmented prostate by registering the second segmented prostate with a surface of interest (SOI) mask.

Method 700 also includes, at 732, generating a patient-specific SOI mesh from registered segmented prostate. The patient-specific SOI mesh includes a plurality of vertices.

Method 700 also includes, at 740, extracting a set of distension features from the patient-specific SOI mesh. The set of distension features includes a Gaussian curvature ($\theta$) feature, a surface normal orientation ($\Phi$) feature represented in a spherical coordinate system, and a $\theta$ kurtosis feature, a $\Phi$ skewness feature, a $\Phi$ standard deviation feature, and a $\Phi$ mean feature computed from the $\theta$ feature and the $\Phi$ feature.

Method 700 also includes, at 742, providing a first machine learning classifier the set of distension features. In one embodiment, the first machine learning classifier is a random forest (RF) classifier having a depth of two and 1000 trees. The first machine learning classifier computes a first probability that the region of tissue will experience PCa recurrence based, at least in part, on the set of distension features. Providing the set of distension features includes acquiring electronic data, reading from a computer file, receiving a computer file, reading from a computer memory, or other computerized activity.

Method 700 also includes, at 750, extracting a set of radiomic features from the first segmented prostate. The set of radiomics features includes a subset of first order statistical features, a subset of Haralick features, and a subset of Gabor features.

Method 700 also includes, at 752, providing a second, different machine learning classifier the set of radiomics features. In one embodiment, the second machine learning classifier is an RF classifier having a depth of two and 1000 trees. The second, different machine learning classifier computes a second probability that the region of tissue will experience PCa recurrence based, at least in part, on the set of radiomics features. Providing the set of radiomics features includes acquiring electronic data, reading from a computer file, receiving a computer file, reading from a computer memory, or other computerized activity.

Method 700 also includes, at 760, receiving, from the first machine learning classifier, the first probability that the region of tissue will experience PCa recurrence. Method 700 also includes, at 762, receiving, from the second machine learning classifier, the second probability that the region of tissue will experience PCa recurrence.

Method 700 also includes, at 770, computing a combined probability that the region of tissue will experience PCa recurrence based on the first probability and the second probability. In one embodiment, the combined probability is computed as $p(F_S, F_S | \omega_+)$ as defined above in Eq. 1. The combined probability may be expressed in Bayesian terms as defined in Eq. 2 above.

Method 700 also includes, at 780, detecting if the combined probability is greater than a threshold probability. In one embodiment, the threshold probability is 0.5. In another embodiment, other threshold probability values may be used. Upon detecting that the combined probability is greater than the threshold probability, method 700, at 784, includes classifying the region of tissue as likely to experience PCa recurrence. Upon detecting that the combined probability is less than or equal to the threshold probability, method 700 includes, at 786, classifying the region of tissue as unlikely to experience PCa recurrence. In another embodiment, method 700 includes, using other conditions (e.g., detecting if the combined probability is greater than or equal to the threshold probability, detecting if the combined probability is less than the threshold probability) to classify the region of tissue.

Method 700 further includes, at 790, displaying the classification. Method 700 may, at 790, also include displaying at least one of the combined probability, the first probability, the second probability, the set of radiomics features, the set of distension features, the first pre-treatment radiological image, or the second pre-treatment radiological image.

In another embodiment, method 700 further includes generating a cancer treatment plan. The cancer treatment plan is based, at least in part, on the classification, and at least one of the combined probability, the set of distension features, the set of radiomics features, or the first pre-treatment radiological image or the second pre-treatment radiological image. In one embodiment, the cancer treatment plan defines an immunotherapy agent dosage or schedule. In another embodiment, the cancer treatment plan defines a chemotherapy treatment agent or schedule, or defines a surgical procedure (e.g., biopsy, prostatectomy).

Figure 8:
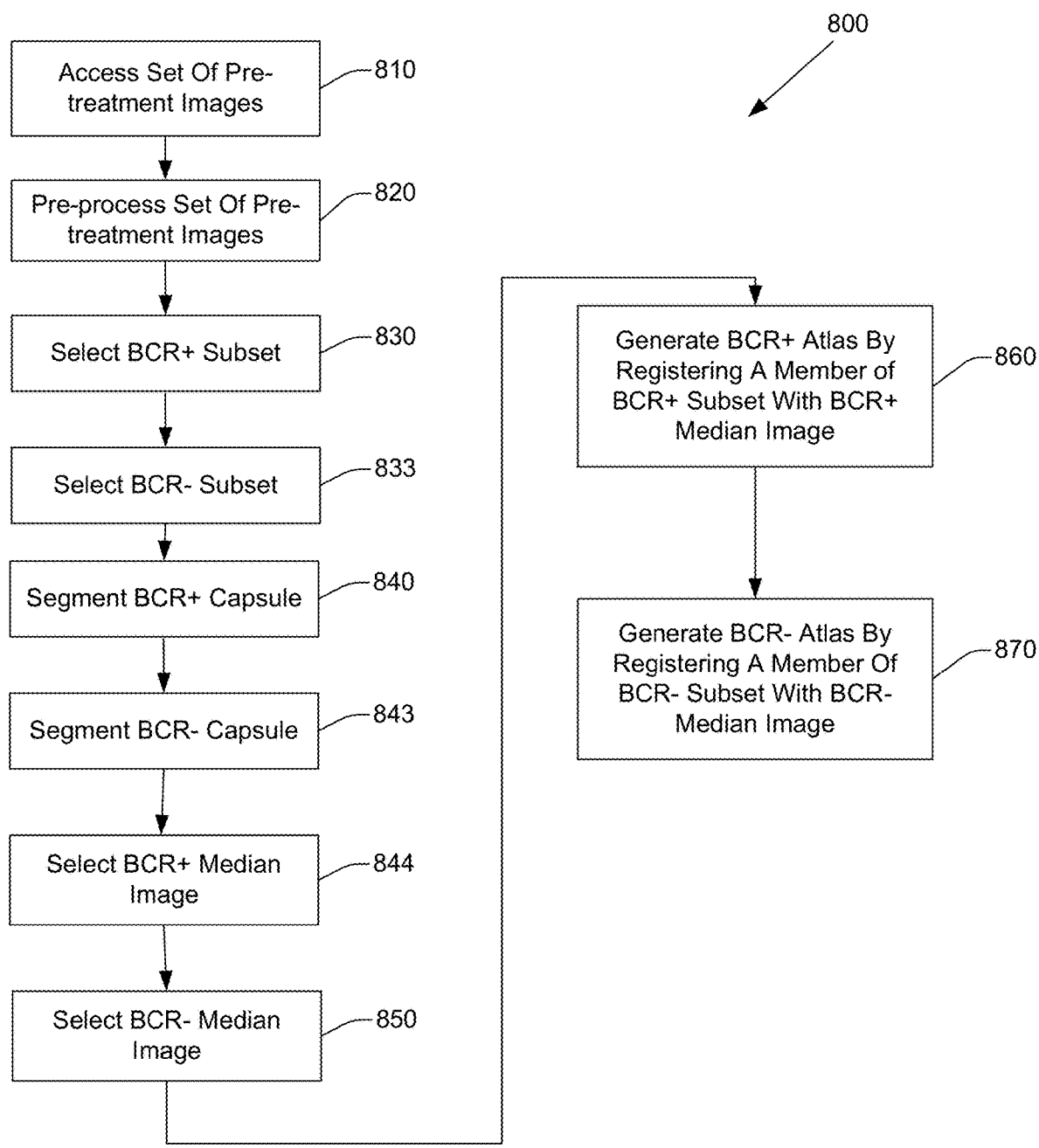
FIG. 8 illustrates an example method for generating a BCR atlas.

In one embodiment, method 700 further includes generating a BCR+ (e.g., C+, A+) atlas, and a BCR− (e.g., C−, A−) atlas. FIG. 8 illustrates an example method 800 for generating a BCR+ atlas and a BCR− atlas that is suitable for implementation by methods, apparatus, processors, and other embodiments described herein, including apparatus 500, apparatus 600, or method 700. Method 800 includes, at 810, accessing a set of pre-treatment images of a region of tissue demonstrating PCa. Accessing the set of pre-treatment images includes acquiring electronic data, reading from a computer file, receiving a computer file, reading from a computer memory, or other computerized activity. The set of pre-treatment images includes a plurality of BCR+ images, and a plurality of BCR− images. In one embodiment, a first region of tissue represented in a first member of the set of pre-treatment images has a Gleason score within a threshold of a second region of tissue represented in a second, different member of the set of pre-treatment images. In this embodiment, first region of tissue has a tumor stage within a threshold of the second region of tissue. Members of the set of pre-treatment images may be T1W or T2W MRI images. In another embodiment, members of the set of pre-treatment images may be acquired using other, different imaging modalities.

Method 800 also includes, at 820, generating a pre-processed set by pre-processing the set of pre-treatment images. In one embodiment, pre-processing the set of pre-treatment images includes using N4 bias field correction to reduce magnetic bias. In another embodiment, other pre-processing techniques may be employed.

Method 800 also includes, at 830, selecting a BCR+ subset from the pre-processed set. Method 800 also includes, at 833, selecting a BCR− subset from the pre-processed set. In one embodiment, the BCR+ subset and the BCR− subset are the same size. In another embodiment, the BCR+ subset and the BCR− subset are within a threshold of the same size. In one embodiment, the availability of complete image datasets (including T1w, T2w and ADC maps), absence of treatment for PCa before MRI, presence of clinically localized PCa, Gleason score available from pretreatment biopsy and/or from radical prostatectomy specimens, and post-treatment outcome data including post-treatment PSA and a minimum of 3 years of follow-up may be used as inclusion criteria for selection into the BCR+ subset or the BCR− subset.

Method 800 also includes, at 840, segmenting a prostate capsule represented in a member of the BCR+ subset. Method 800 also includes, at 843, segmenting a prostate capsule represented in a member of the BCR− subset. In one embodiment, a statistical shape and appearance model-based segmentation technique is employed. In another embodiment, other segmentation techniques may be employed.

Method 800 also includes, at 850, selecting a BCR+ median image from the BCR+ subset. Method 800 also includes, at 853, selecting a BCR− median image from the BCR− subset. Selecting a BCR+ median image or a BCR− median image includes selecting the BCR+ image or BCR− image that includes the prostate with the median volume for the respective subset.

Method 800 also includes, at 860, generating a BCR+ atlas by registering a member of the BCR+ subset to the BCR+ median image. Method 800 further includes, at 870, generating a BCR− atlas by registering a member of the BCR− subset to the BCR− median image.

Figure 9:
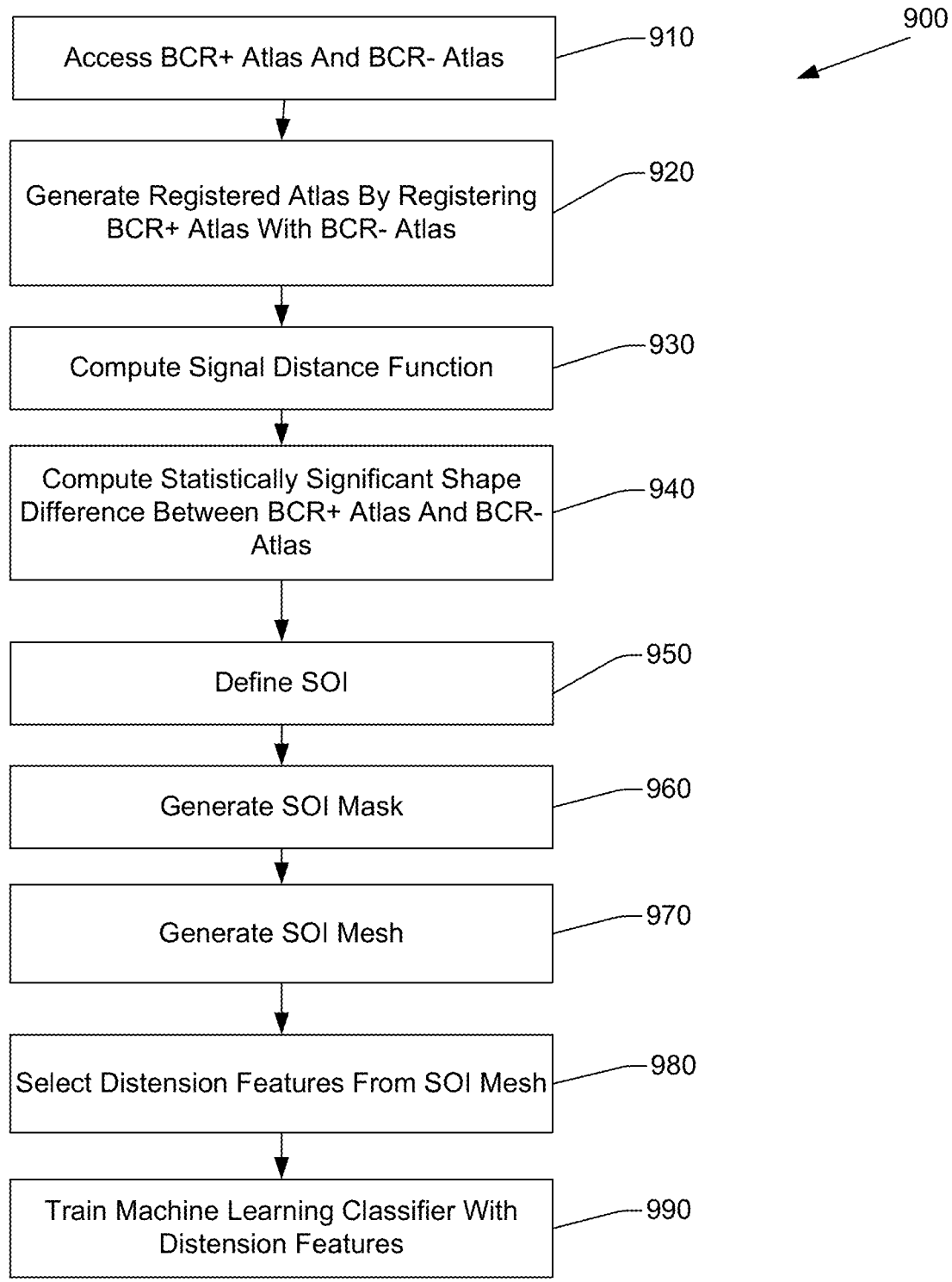
FIG. 9 illustrates an example method for training a machine learning classifier to predict BCR.

In one embodiment, method 700 or method 800 may further include training the machine learning classifier. FIG. 9 illustrates an example method 900 for training a machine learning classifier to predict BCR that is suitable for use by example methods, apparatus, processors, systems, and other embodiments described herein. Method 900 includes, at 910, accessing a BCR+ atlas and a BCR− atlas. Accessing the BCR+ atlas and the BCR− atlas includes acquiring electronic data, reading from a computer file, receiving a computer file, reading from a computer memory, or other computerized activity.

Method 900 also includes, at 920, generating a registered atlas by registering the BCR+ atlas with the BCR− atlas.

Method 900 also includes, at 930, computing a signal distance function from the registered atlas.

Method 900 also includes, at 940, computing statistically significant shape differences between the BCR+ atlas and the BCR− atlas. Method 900 computes the statistically significant shape differences based, at least in part, on the registered atlas and the signal distance function.

Method 900 also includes, at 950, defining an SOI based on the statistically significant shape differences.

Method 900 also includes, at 960, generating an SOI mask from the SOI.

Method 900 also includes, at 970, generating an SOI mesh from the SOI mask. The SOI mesh includes a plurality of vertices. Distension features (e.g., shape features, FOrge features) may be extracted from a vertex of the SOI mesh.

Method 900 also includes, at 980, selecting a set of distension features from the SOI mesh. In one embodiment, distension features are extracted from every vertex in the SOI mesh. In another embodiment, distension features are extracted from a threshold number of vertices. Extracting distension features from a threshold number of vertices less than all the vertices in the SOI mesh may improve the performance of a computer performing methods described herein by reducing the computational complexity relative to conventional approaches which may require extracting features from every vertex.

In one embodiment, the set of distension features is selected using a random forest (RF) Gini impurity index. Selecting the distension features using the RF Gini impurity index facilitates selecting the most discriminative features. In one embodiment, the set of distension features includes a curvature magnitude feature, an XY plane surface normal orientation feature, an XZ plane surface normal orientation feature, a curvature magnitude standard deviation feature, a curvature magnitude range feature, a curvature magnitude mean feature, an XY plane surface normal orientation mean feature, an XY plane surface normal orientation kurtosis feature, an XY plane surface normal orientation range feature, an XY plane surface normal orientation standard deviation feature, an XZ plane surface normal orientation standard deviation feature, and an XZ plane surface normal orientation range feature. In another embodiment, other, different features may be selected based, at least in part, on the RF Gini impurity index, or other selection criterion.

Method 900 further includes, at 990, training the machine learning classifier with the set of distension features. In one embodiment, training the machine learning classifier with the set of distension features includes training the machine learning classifier using three-cross validation. Embodiments may train the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

Improved identification or classification of patients who will experience BCR may produce the technical effect of improving treatment efficacy by increasing the accuracy of and decreasing the time required to treat patients demonstrating BCR in PCa or other forms of cancerous pathology. Treatments and resources, including expensive immunotherapy agents, may be more accurately tailored to patients with a likelihood of benefiting from said treatments and resources, including responding to immunotherapy, so that more appropriate treatment protocols may be employed, and expensive resources are not wasted. Controlling a personalized medicine system, a CADx system, or a cancer BCR or progression prediction system based on improved identification or classification of patients who will experience BCR or progression further improves the operation of the system, since unnecessary operations will not be performed.

Using a more appropriately modulated treatment may lead to less aggressive therapeutics being required for a patient or may lead to avoiding or delaying a biopsy, a resection, or other invasive procedure. When patients experiencing PCa who will more likely experience BCR or progression are more quickly and more accurately distinguished from patients who will not, patients most at risk may receive a higher proportion of scarce resources (e.g., therapeutics, physician time and attention, hospital beds) while those less likely to benefit from the treatment may be spared unnecessary treatment, which in turn spares unnecessary expenditures and resource consumption. Example methods, apparatus, and other embodiments may thus have the additional effect of improving patient outcomes compared to conventional approaches.

While FIGS. 7, 8, and 9 illustrate various actions occurring in serial, it is to be appreciated that various actions illustrated in FIG. 7 could occur substantially in parallel. By way of illustration, a first process could involve segmenting a prostate capsule represented in a pre-treatment MRI image, a second process could involve extracting distension features, and a third process could involve extracting radiomic features. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods described or claimed herein including method 700, 800, or 900. While executable instructions associated with the listed methods are described as being stored on a computer-readable storage device, it is to be appreciated that executable instructions associated with other example methods described or claimed herein may also be stored on a computer-readable storage device. In different embodiments the example methods described herein may be triggered in different ways. In one embodiment, a method may be triggered manually by a user. In another example, a method may be triggered automatically.

Figure 10:
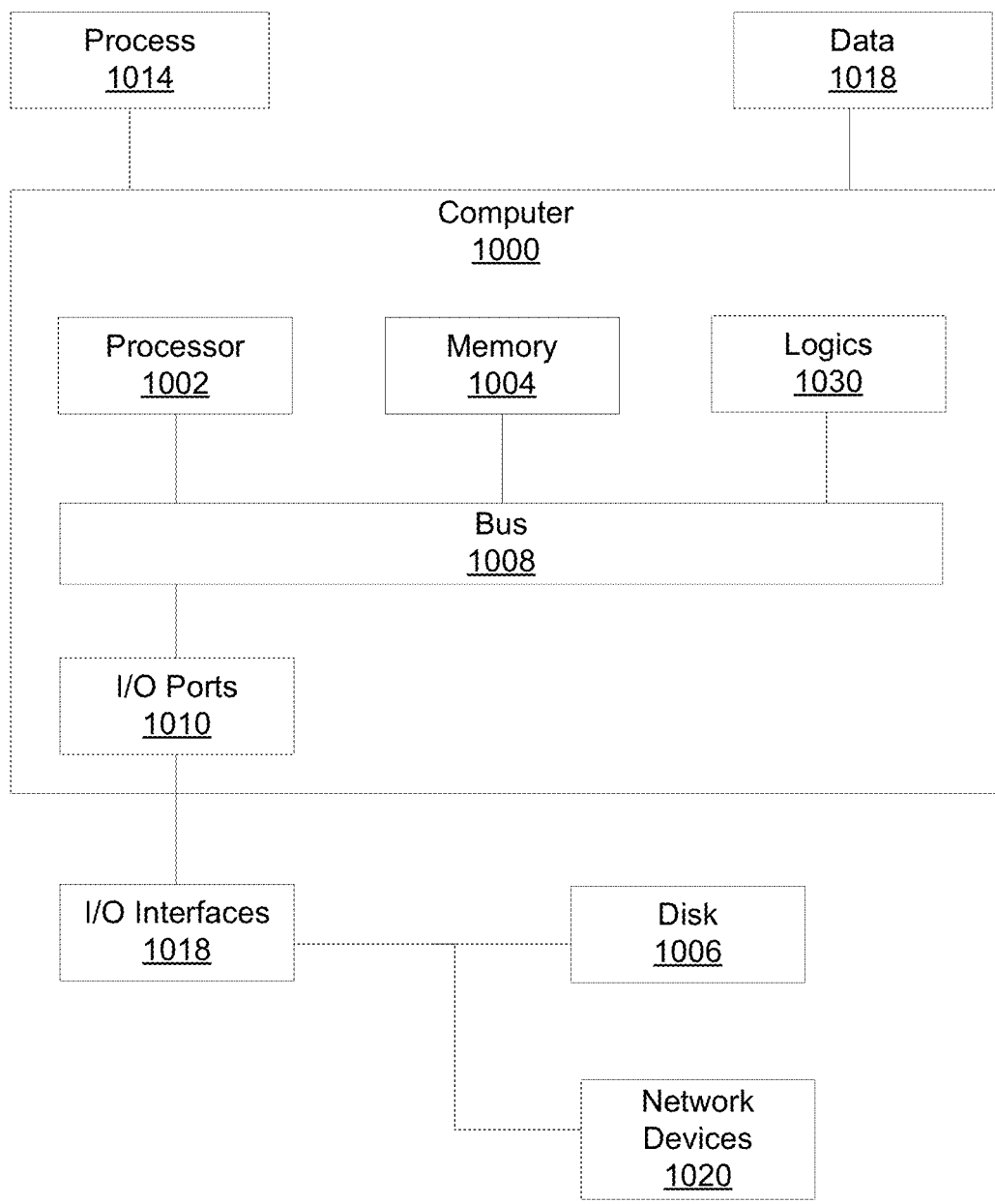
FIG. 10 illustrates an example computer in which example embodiments described herein may operate.

FIG. 10 illustrates an example computer 1000 in which example methods illustrated herein can operate and in which example methods, apparatus, circuits, operations, or logics may be implemented. In different examples, computer 1000 may be part of a personalized medicine system, a cancer progression or recurrence prediction system, a digital whole slide scanner, a CT system, may be operably connectable to a CT system, an MRI system, a personalized medicine system, or a digital whole slide scanner, or may be part of a CADx system.

Computer 1000 includes a processor 1002, a memory 1004, and input/output (I/O) ports 1010 operably connected by a bus 1008. In one example, computer 1000 may include a set of logics or circuits 1030 that perform a method of predicting cancer progression or recurrence using a machine learning classifier. Thus, the set of circuits 1030, whether implemented in computer 1000 as hardware, firmware, software, and/or a combination thereof may provide means (e.g., hardware, firmware, circuits) for predicting cancer BCR based on combined distension and radiomics features extracted from MRI imagery. In different examples, the set of circuits 1030 may be permanently and/or removably attached to computer 1000.

Processor 1002 can be a variety of various processors including dual microprocessor and other multi-processor architectures. Processor 1002 may be configured to perform steps of methods claimed and described herein. Memory 1004 can include volatile memory and/or non-volatile memory. A disk 1006 may be operably connected to computer 1000 via, for example, an input/output interface (e.g., card, device) 1018 and an input/output port 1010. Disk 1006 may include, but is not limited to, devices like a magnetic disk drive, a tape drive, a Zip drive, a flash memory card, or a memory stick. Furthermore, disk 1006 may include optical drives like a CD-ROM or a digital video ROM drive (DVD ROM). Memory 1004 can store processes 1014 or data 1017, for example. Data 1017 may, in one embodiment, include digitized MRI images of a region of tissue demonstrating PCa. Disk 1006 or memory 1004 can store an operating system that controls and allocates resources of computer 1000.

Bus 1008 can be a single internal bus interconnect architecture or other bus or mesh architectures. While a single bus is illustrated, it is to be appreciated that computer 800 may communicate with various devices, circuits, logics, and peripherals using other buses that are not illustrated (e.g., PCIE, SATA, Infiniband, 1394, USB, Ethernet).

Computer 1000 may interact with input/output devices via I/O interfaces 1018 and input/output ports 810. Input/output devices can include, but are not limited to, CT systems, MRI systems, digital whole slide scanners, an optical microscope, a keyboard, a microphone, a pointing and selection device, cameras, video cards, displays, disk 1006, network devices 1020, or other devices. Input/output ports 1010 can include but are not limited to, serial ports, parallel ports, or USB ports.

Computer 1000 may operate in a network environment and thus may be connected to network devices 1020 via I/O interfaces 1018 or I/O ports 1010. Through the network devices 1020, computer 1000 may interact with a network. Through the network, computer 1000 may be logically connected to remote computers. The networks with which computer 1000 may interact include, but are not limited to, a local area network (LAN), a wide area network (WAN), or other networks, including the cloud.

Examples herein can include subject matter such as an apparatus, a personalized medicine system, a CADx system, a processor, a system, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting cancer recurrence, or cancer progression, according to embodiments and examples described.

One example embodiment includes a computer-readable storage device storing computer-executable instructions that, in response to execution, cause a BCR prediction system, a CADx system, a personalized medicine system, or a processor, to perform operations. The operations may include accessing a first pre-treatment image of a region of tissue demonstrating prostate cancer (PCa), where the first pre-treatment image includes a segmented prostate capsule, and accessing a second pre-treatment image of the region of tissue, where the second pre-treatment image includes the prostate capsule. The images include a plurality of voxels, a voxel having an intensity. The images may be digitized three-dimensional (3D) pre-treatment MRI image of a region of tissue demonstrating PCa, where the image includes a segmented prostate capsule. In another embodiment, the image is a pre-treatment image of a region of tissue demonstrating another, different type of cancer.

A BCR prediction system, a personalized medicine system, or a processor may include circuitry such as, but not limited to, one or more single-core or multi-core processors. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The operations may also include accessing a first pre-treatment image of a region of tissue demonstrating prostate cancer (PCa), where the first pre-treatment image includes a segmented prostate capsule;

The operations may also include accessing a second pre-treatment image of the region of tissue, where the pre-treatment image includes the segmented prostate capsule;

The operations may also include generating a registered segmented prostate capsule by registering the segmented prostate capsule represented in the first pre-treatment image to a recurrence negative (C−) median template. In one embodiment, registering the segmented prostate capsule with the C− median template includes registering the segmented prostate capsule with the C− median template using a rigid registration technique.

The operations may also include registering a surface of interest (SOI) mask to the registered segmented prostate capsule. In one embodiment, registering the SOI mask with the registered segmented prostate includes registering the SOI mask with the registered segmented prostate using a B-spline registration technique.

The operations may also include generating a patient-specific SOI mask from the registered SOI mask.

The operations may also include generating a patient-specific SOI mesh from the patient-specific SOI mask;

The operations may also include extracting a set of field effect induced organ distension features from the patient-specific mesh. In one embodiment, the set of organ distension features a Gaussian curvature ($\theta$) feature, a surface normal orientation ($\Phi$) feature represented in a spherical coordinate system, and a $\theta$ kurtosis feature, a $\Phi$ skewness feature, a $\Phi$ standard deviation feature, and a $\Phi$ mean feature computed from the $\theta$ feature and the $\Phi$ feature.

The operations may also include computing a first probability that the region of tissue will experience PCa recurrence based, at least in part, on the set of organ distension features. Computing the probability may include, in one embodiment, providing the organ distension features to a first machine learning classifier. Providing the organ distension features to a machine learning classifier includes acquiring electronic data, reading from a computer file, receiving a computer file, reading from a computer memory, or other computerized activity. In one embodiment, the first machine learning classifier is a random forest classifier. In this embodiment, the first machine learning classifier computes a first probability that the region of tissue will experience BCR based, at least in part on the organ distension features. In one embodiment, the operations further include training the first machine learning classifier. In one embodiment, the operations further include testing the first machine learning classifier on a held-out testing dataset. In another embodiment, the first machine learning classifier may be an SVM, a QDA classifier, an LDA classifier, a CNN, or other type of machine learning classifier.

The operations may also include extracting a set of radiomic features from the segmented prostate capsule represented in the second pre-treatment image. The set of radiomic features includes a subset of first order statistical features, a subset of Haralick features, a subset of Gabor features, and a subset of C0L1AGe features.

The operations may also include computing a second probability that the region of tissue will experience PCa recurrence based, at least in part, on the set of radiomics features;

The operations may also include computing a joint-probability that the region of tissue will experience PCa recurrence based on the first probability and the second probability;

The operations may also include classifying the region of tissue as likely to experience BCR or unlikely to experience BCR based, at least in part, on the joint probability. In one embodiment, the region of tissue is classified as likely to experience BCR when the joint probability has a value of 0.5 or greater. In another embodiment, the region of tissue is classified as likely to experience BCR when the joint probability has another, different value. In one embodiment, the region of tissue is classified with an AUC of at least 0.84. In another embodiment, the operations include generating a classification of the region of tissue as likely to experience cancer progression or unlikely to experience cancer recurrence based, at least in part, on the joint probability.

The operations may also include displaying the classification, the joint probability, the set of organ distension features, the set of radiomic features, the patient-specific SOI mesh, the patient-specific SOI mask, the first pre-treatment image, or the second pre-treatment image.[/end new claim]

The operations may further include generating a cancer treatment plan based, at least in part, on the classification, and at least one of the joint probability, the set of organ distension features, or the set of radiomics features. In one embodiment, the cancer treatment plan may include an immunotherapy agent dosage or schedule, a chemotherapy agent dosage or schedule, or a surgical procedure plan.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. An apparatus for predicting prostate cancer (PCa) recurrence, the apparatus comprising:
a processor;
a memory;
an input/output (I/O) interface;
a set of circuits including an image acquisition circuit, a segmentation circuit, a registration circuit, a distension feature circuit, a radiomics circuit, a combined tumor induced organ distension with tumor radiomics (COnTRa) circuit, and a display circuit; and
an interface that connects the processor, the memory, the I/O interface, and the set of circuits;
where the memory is configured to store a first pre-treatment image of a region of tissue demonstrating PCa, a second pre-treatment image of the region of tissue, a recurrence-negative (C−) median template, and a surface of interest (SOI) mask, where the region of tissue includes a prostate capsule, the first pre-treatment image having a plurality of voxels, and the second pre-treatment image having a plurality of voxels, a voxel having an intensity;
where the image acquisition circuit is configured to access the first pre-treatment image and the second pre-treatment image;
where the segmentation circuit is configured to:
generate a first segmented prostate by segmenting the prostate capsule represented in the first pre-treatment image, and;
generate a second segmented prostate by segmenting the prostate capsule represented in the second pre-treatment image;
where the registration circuit is configured to:
generate a registered prostate by registering the first segmented prostate with the SOI mask;
generate a patient-specific SOI mask from the registered prostate and the SOI mask; and
generate a patient-specific SOI mesh from the patient-specific SOI mask;
where the distension feature circuit is configured to:
extract a set of distension features from the patient-specific SOI mesh; and
compute a first probability of PCa recurrence based on the set of distension features;
where the radiomics circuit is configured to:
extract a set of radiomics features from the second pre-treatment image; and
compute a second probability of PCa recurrence based on the set of radiomics feature;

where the COnTRa circuit is configured to:
compute a joint probability that the region of tissue will experience PCa recurrence based on the first probability and the second probability; and
where the display circuit is configured to display the joint probability.

2. The apparatus of claim 1, where the SOI mask is a spatially contextual surface of interest that defines a region of differential distension between recurrence-positive (C+) and C− regions of tissue.

3. The apparatus of claim 1, where the first pre-treatment image is a T2w magnetic resonance imaging (MRI) image of a region of tissue demonstrating PCa.

4. The apparatus of claim 1, where the second pre-treatment image is a T2w apparent diffusion coefficient (ADC) dynamic contrast enhanced (DCE) MRI image of the region of tissue.

5. The apparatus of claim 1, where the registration circuit is configured to register the SOI mask with the first pre-treatment image using an affine registration technique and a B-spline registration technique.

6. The apparatus of claim 1, where the patient-specific SOI mesh includes a plurality of vertices.

7. The apparatus of claim 1, where the set of distension features includes a Gaussian curvature ($\theta$) feature, and a surface normal orientation ($\Phi$) feature represented in a spherical coordinate system.

8. The apparatus of claim 7, where the set of distension features further includes a $\theta$ kurtosis feature, a $\Phi$ skewness feature, a $\Phi$ standard deviation feature, and a $\Phi$ mean feature computed from the $\theta$ feature and the $\Phi$ feature.

9. The apparatus of claim 1, where the distension feature circuit further comprises a machine learning component configured to compute the first probability based on the set of distension features.

10. The apparatus of claim 9, where the machine learning component is configured as a random forest (RF) classifier having a depth of two and 1000 trees.

11. The apparatus of claim 1, where the set of radiomics features includes a subset of first order statistical features, a subset of Haralick features, and a subset of Gabor features.

12. The apparatus of claim 1, where the radiomics circuit further comprises a machine learning component configured to compute the second probability based on the set of radiomics features.

13. The apparatus of claim 12, where the machine learning component is configured as a random forest (RF) classifier having a depth of two and 1000 trees.

14. The apparatus of claim 1, the set of circuits further comprising an atlas circuit configured to:
generate a recurrence-positive (C+) atlas;
generate a C− atlas;
generate a registered atlas by registering the C+ atlas with the C− atlas; and
generate the SOI mask from the registered atlas.

15. A non-transitory computer-readable storage device storing computer executable instructions that when executed by a computer control the computer to perform a method for predicting prostate cancer (PCa) recurrence, the method comprising:
accessing a first pre-treatment radiological image of a region of tissue demonstrating PCa;
accessing a second pre-treatment radiological image of the region of tissue;
generating a first segmented prostate by automatically segmenting a prostate capsule represented in the first pre-treatment radiological image;
generating a second segmented prostate by automatically segmenting the prostate capsule represented in the first pre-treatment radiological image;
generating a registered segmented prostate by registering the first segmented prostate with a surface of interest (SOI) mask;
generating a patient-specific SOI mesh from registered segmented prostate;
extracting a set of distension features from the patient-specific SOI mesh;
providing a first machine learning classifier the set of distension features;
extracting a set of radiomic features from the second segmented prostate;
providing a second machine learning classifier the set of radiomic features;
receiving, from the first machine learning classifier, a first probability that the region of tissue will experience PCa recurrence based, at least in part, on the set of distension features;
receiving, from the second machine learning classifier, a second probability that the region of tissue will experience PCa recurrence based, at least in part, on the set of radiomic features;
computing a combined probability that the region of tissue will experience PCa recurrence based on the first probability and the second probability;
upon detecting that the combined probability is greater than a threshold probability:
classifying the region of tissue as likely to experience PCa recurrence;
upon detecting that the combined probability is less than or equal to the threshold probability:
classifying the region of tissue as unlikely to experience PCa recurrence;
displaying the classification and at least one of the combined probability, the first probability, the second probability, the set of radiomics features, the set of distension features, the first pre-treatment radiological image, or the second pre-treatment radiological image.

16. The non-transitory computer-readable storage device of claim 15, where the first pre-treatment radiological image is a T2w apparent diffusion coefficient (ADC) dynamic contrast enhanced (DCE) magnetic resonance imaging (MRI) image of the region of tissue, and where the second pre-treatment radiological image is a T2w MRI image.

17. The non-transitory computer-readable storage device of claim 15, where the set of radiomics features includes a subset of first order statistical features, a subset of Haralick features, and a subset of Gabor features.

18. The non-transitory computer-readable storage device of claim 15, where the set of distension features includes a Gaussian curvature ($\theta$) feature, a surface normal orientation ($\Phi$) feature represented in a spherical coordinate system, and a $\theta$ kurtosis feature, a $\Phi$ skewness feature, a $\Phi$ standard deviation feature, and a $\Phi$ mean feature computed from the $\theta$ feature and the $\Phi$ feature.

19. The non-transitory computer-readable storage device of claim 15, where the first machine learning classifier is a random forest (RF) classifier having a depth of two and 1000 trees, and where the second machine learning classifier is a random forest (RF) classifier having a depth of two and 1000 trees.

20. A non-transitory computer-readable storage device storing instructions that when executed by a processor control the processor to perform operations, the operations including:

accessing a first pre-treatment image of a region of tissue demonstrating prostate cancer (PCa), where the first pre-treatment image includes a segmented prostate capsule;
accessing a second pre-treatment image of the region of tissue, where the second pre-treatment image includes the segmented prostate capsule;
generating a registered segmented prostate capsule by registering the segmented prostate capsule represented in the first pre-treatment image to a recurrence negative (C−) median template;
registering a surface of interest (SOI) mask to the registered segmented prostate capsule;
generating a patient-specific SOI mask from the registered SOI mask;
generating a patient-specific SOI mesh from the patient-specific SOI mask;
extracting a set of organ distension features from the patient-specific mesh, where the set of organ distension features a Gaussian curvature ($\theta$) feature, a surface normal orientation ($\Phi$) feature represented in a spherical coordinate system, and a $\theta$ kurtosis feature, a $\Phi$ skewness feature, a $\Phi$ standard deviation feature, and a $\Phi$ mean feature computed from the $\theta$ feature and the $\Phi$ feature;
computing a first probability that the region of tissue will experience PCa recurrence based, at least in part, on the set of organ distension features;
extracting a set of radiomic features from the segmented prostate capsule represented in the second pre-treatment image, where the set of radiomic features includes a subset of first order statistical features, a subset of Haralick features, and a subset of Gabor features;
computing a second probability that the region of tissue will experience PCa recurrence based, at least in part, on the set of radiomics features;
computing a joint-probability that the region of tissue will experience PCa recurrence based on the first probability and the second probability;
classifying the region of tissue as likely to experience biochemical recurrence (BCR) or unlikely to experience BCR based, at least in part, on the joint probability; and
displaying the classification, the joint probability, the set of organ distension features, the set of radiomic features, the patient-specific SOI mesh, the patient-specific SOI mask, the first pre-treatment image, or the second pre-treatment image.

* * * * *